US009545379B2

(12) United States Patent
Liu et al.

(10) Patent No.: US 9,545,379 B2
(45) Date of Patent: Jan. 17, 2017

(54) FORMULATIONS AND METHODS FOR CONTEMPORANEOUS STABILIZATION OF ACTIVE PROTEINS DURING SPRAY DRYING AND STORAGE

(71) Applicant: Velico Medical, Inc., Beverly, MA (US)

(72) Inventors: Qiyong Peter Liu, Newton, MA (US); Junqing Cui, West Roxbury, MA (US); Rud Karly Lucien, Lynn, MA (US); Ryan Carney, Hudson, NH (US); Jihae Sohn, Brighton, MA (US); Michelle Arya, Medford, MA (US)

(73) Assignee: Velico Medical, Inc., Beverly, MA (US)

( * ) Notice: Subject to any disclaimer, the term of this patent is extended or adjusted under 35 U.S.C. 154(b) by 0 days.

(21) Appl. No.: 14/858,539

(22) Filed: Sep. 18, 2015

(65) Prior Publication Data

US 2016/0082044 A1 Mar. 24, 2016

Related U.S. Application Data

(60) Provisional application No. 62/052,689, filed on Sep. 19, 2014.

(51) Int. Cl.

| | |
|---|---|
| *A61K 35/16* | (2015.01) |
| *A61K 35/15* | (2015.01) |
| *A61K 35/14* | (2015.01) |
| *A61K 9/16* | (2006.01) |
| *F26B 3/06* | (2006.01) |
| *F26B 5/04* | (2006.01) |
| *F26B 3/12* | (2006.01) |

(52) U.S. Cl.
CPC ............... *A61K 9/16* (2013.01); *A61K 9/1682* (2013.01); *A61K 9/1688* (2013.01); *F26B 3/06* (2013.01); *F26B 3/12* (2013.01); *F26B 5/04* (2013.01)

(58) Field of Classification Search
CPC .......... A61K 35/14; A61K 35/16; A61K 9/16; A61K 9/1682
USPC ..................................... 424/530, 529; 435/2
See application file for complete search history.

(56) References Cited

U.S. PATENT DOCUMENTS

| | | | | |
|---|---|---|---|---|
| 2,575,175 A * | 11/1951 | Kronisch | A61K 35/16 204/157.68 |
| 5,252,221 A * | 10/1993 | van Dommelen | A23J 1/06 210/645 |
| 7,297,716 B2 | 11/2007 | Shanbrom | |
| 7,931,919 B2 | 4/2011 | Bakaltcheva et al. | |
| 7,993,310 B2 | 8/2011 | Rosiello | |
| 8,434,242 B2 | 5/2013 | Hubbard et al. | |
| 8,518,452 B2 | 8/2013 | Bjornstrup et al. | |
| 8,533,971 B2 | 9/2013 | Hubbard, Jr. et al. | |
| 8,533,972 B2 | 9/2013 | Hubbard, Jr. et al. | |
| 8,595,950 B2 | 12/2013 | Hubbard, Jr. et al. | |
| 8,601,712 B2 | 12/2013 | Hubbard, Jr. et al. | |
| 2004/0058309 A1* | 3/2004 | Washizu | A61K 31/198 435/2 |
| 2004/0086420 A1* | 5/2004 | MacPhee | A61L 2/0011 422/22 |
| 2007/0166389 A1* | 7/2007 | Bakaltcheva | A01N 1/02 424/532 |
| 2008/0145834 A1* | 6/2008 | Ho | A01N 1/02 435/2 |
| 2009/0223080 A1* | 9/2009 | McCarthy | A61J 1/10 34/284 |
| 2010/0108183 A1 | 5/2010 | Rosiello | |
| 2010/0233671 A1* | 9/2010 | Bakaltcheva | A61K 9/0019 435/2 |
| 2010/0273141 A1* | 10/2010 | Bakaltcheva | A61K 35/16 435/2 |
| 2011/0142885 A1 | 6/2011 | Haley et al. | |
| 2012/0167405 A1* | 7/2012 | Hubbard, Jr. | F26B 3/12 34/82 |
| 2013/0000774 A1 | 1/2013 | Rosiello | |
| 2013/0126101 A1 | 5/2013 | Hubbard, Jr. et al. | |
| 2013/0209985 A1* | 8/2013 | Hoke | A61B 5/1438 435/2 |
| 2013/0243877 A1* | 9/2013 | Haley | A61K 35/16 424/530 |
| 2014/0083627 A1 | 3/2014 | Khan et al. | |
| 2014/0083628 A1 | 3/2014 | Khan et al. | |
| 2014/0088768 A1 | 3/2014 | Haley et al. | |
| 2016/0082043 A1 | 3/2016 | Khan et al. | |

FOREIGN PATENT DOCUMENTS

| | | |
|---|---|---|
| CN | 102206273 * | 10/2011 |
| WO | 2005079755 A2 | 9/2005 |

OTHER PUBLICATIONS

Lea, et al. "The Reaction between Proteins and Reducing Sugars in the "Dry" State" Department of Pathology, University of Cambridge; Jun. 5, 1950; pp. 626-629.

Carpenter, et al. "Rational Design of Stable Lyophilized Protein Formulations: Theory and Practice" Kluwer Academic/Plenum Publishers; 2002; pp. 109-133.

(Continued)

*Primary Examiner* — Chris R Tate

(74) *Attorney, Agent, or Firm* — Pierce Atwood LLP; Kevin M. Farrell; David J. Wilson

(57) ABSTRACT

A method of treatment of plasma with a physiologically compatible spray dry stable acidic substance (SDSAS) prior to or contemporaneously with spray drying of the plasma that results in greater recovery and greater long-term stabilization of the dried plasma proteins as compared to spray dried plasma that has not be subject to the formulation method of the present invention, as well as compositions related to plasma dried by the methods of the present invention.

20 Claims, 18 Drawing Sheets

(56) References Cited

OTHER PUBLICATIONS

Schmid "Spray drying of protein precipitates and Evaluation of the Nano Spray Dryer B-90" PhD Thesis; 2011; 125 pages.

Shuja, et al. "Development and Testing of Low-Volume Hyperoncotic, Hyperosmotic Spray-Dried Plasma for the Treatment of Trauma-Associated Coagulopathy" The Journal of Trauma; Mar. 2011; vol. 70; No. 3; pp. 664-671.

Bakaltcheva; et al. "Freeze-dried whole plasma: Evaluating sucrose, trehalose, sorbitol, mannitol and glycine as stabilizers" Thrombosis Research; 2007; vol. 120; pp. 105-116.

* cited by examiner

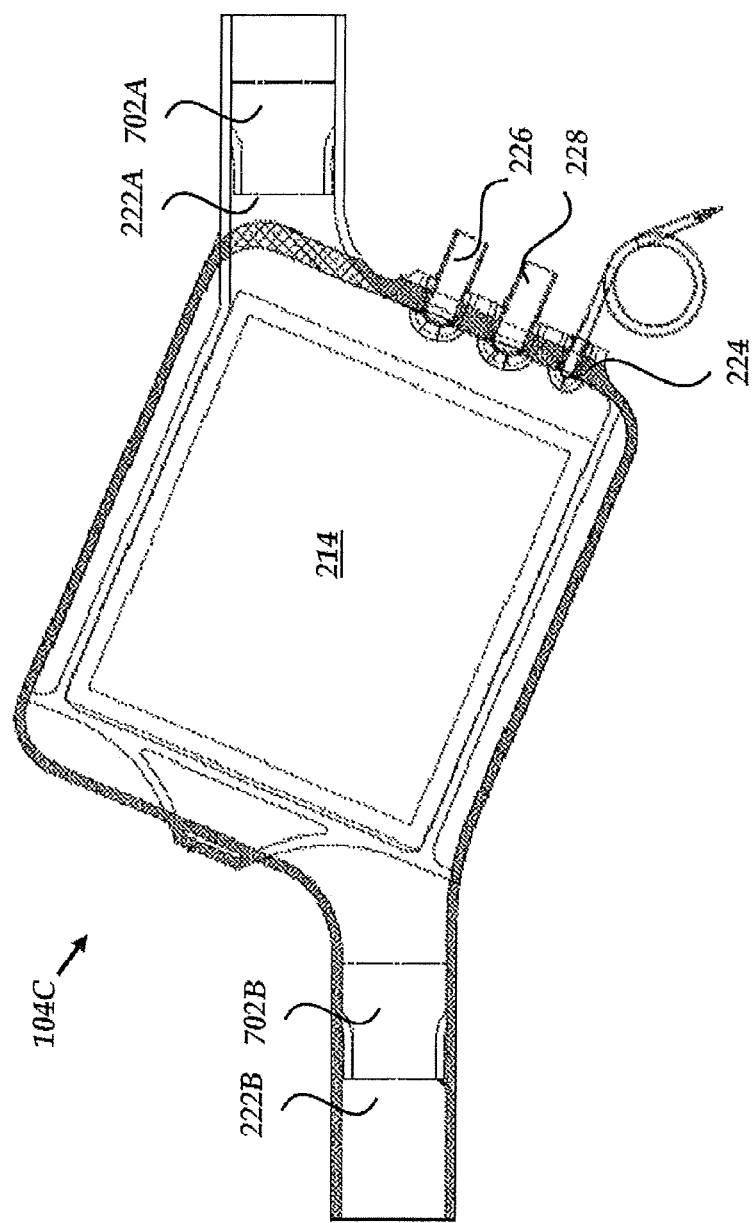

Lane
13  Type 2B vWD Control
14  Healthy Control
15  CP (naïve FFP)
16  CP/PreT
17  SpDP
18  SpDP/PreT

FORMULATIONS AND METHODS FOR CONTEMPORANEOUS STABILIZATION OF ACTIVE PROTEINS DURING SPRAY DRYING AND STORAGE

GOVERNMENT SUPPORT

This invention was made with Government support under contract HHS0100201200005C awarded by the Biomedical Advanced Research and Development Authority (BARDA). The Government has certain rights in the invention.

BACKGROUND

Making up about 55% of the total volume of whole blood, blood plasma is a whole blood component in which blood cells and other constituents of whole blood are suspended. Blood plasma further contains a mixture of over 700 proteins and additional substances that perform functions necessary for bodily health, including clotting, protein storage, and electrolytic balance, amongst others. When extracted from whole blood, blood plasma may be employed to replace bodily fluids, antibodies and clotting factors. Accordingly, blood plasma is extensively used in medical treatments.

To facilitate storage and transportation of blood plasma until use, plasma is typically preserved by freezing soon after its collection from a donor. Fresh-Frozen Plasma (FFP) is obtained through a series of steps involving centrifugation of whole blood to separate plasma and then freezing the collected plasma within less than 8 hours of collecting the whole blood. In the United States, the American Association of Blood Banks (AABB) standard for storing FFP is up to 12 months from collection when stored at a temperature of −18° C. or below. FFP may also be stored for up to 7 years from collection if maintained at a temperature of −65° C. or below. In Europe, FFP has a shelf life of only 3 months if stored at temperatures between −18° C. to −25° C., and for up to 36 months if stored at colder than −25° C. If thawed, European standards dictate that the plasma must be transfused immediately or stored at 1° C. to 6° C. and transfused within 24 hours. If stored longer than 24 hours, the plasma must be relabeled for other uses or discarded.

Notably, however, FFP must be kept in a temperature-controlled environment of −18° C. or colder throughout its duration of storage to prevent degradation of certain plasma proteins and maintain its efficacy, which adds to the cost and difficulty of storage and transport. Furthermore, FFP must be thawed prior to use, resulting in a delay of 30-80 minutes before it may be used after removal from cold storage.

Accordingly, there is a need to develop alternative techniques for the processing and storage of plasma.

SUMMARY

A long-standing need and challenge to the blood industry has been to provide safe, reliable and convenient blood products while preserving the efficacy and safety of those products in storage and when used in transfusion or as a source for medical treatments. The present invention provides efficacy preservation and includes the preservation of the clotting factors in the plasma in a manner that does not otherwise harm the plasma or the transfused patient. During spray drying, some blood plasma proteins degrade to some extent, due to shear stress, surface stress (e.g., air-liquid interfacial stress), exposure to extreme pH, thermal stress, dehydration stress, and other environmental stresses.

The methods and compositions of the present invention recognize that pH and associated stresses can be reduced or the effects of which can be ameliorated by the use of novel formulations of the liquid plasma prior to or contemporaneously with spray drying. Formulation of the liquid plasma by citric acid or a similar spray dry stable acidic substance (SDSAS), at novel concentrations, maintains the pH of the plasma at a non-alkaline level during the spray drying process. This results in higher recovery and better subsequent storage stability of active plasma proteins when compared to unformulated plasma. FIGS. 4 A-C show how the SDSAS of the present invention may be added (formulated) contemporaneously with the plasma in the spray drying process.

The term "recovery" is defined herein as referring to the percentage of an analyte preserved after spray drying compared with the analyte in a sample of the same native plasma (the same sample before spray drying); the analyte is analyzed on native plasma and rehydrated plasma at the same protein concentrations. The analyte can be any known plasma substance such as a protein (e.g., vWF antigen or fibrinogen) and can be measured by concentration or activity of the analyte (e.g., vWF:RCo activity).

A spray dry stable acidic substance (SDSAS) as used herein is any substance such as an acid or acidic salt or other substance that effectuates pH and is physiologically suitable for addition to the plasma being spray dried and physiologically suitable to the subjects (human or otherwise) to which the reconstituted plasma is to be administered (transfused). The SDSAS remains sufficiently stable (e.g., does not materially evaporate or chemically breakdown) during the spray drying process. The SDSAS effectuates the pH adjustment described herein which results, for example, in improved von Willebrand's factor recovery in the reconstituted plasma described herein. Specific examples known to the inventors of spray dry stable acidic substances include citric acid, lactic acid, monosodium citrate, glycine HCL and other SDSAS's described herein. Other SDSAS's may be known in the art or may be determinable by straightforward experimentation.

Accordingly, spray drying formulation, i.e., treatment of feed plasma prior to or contemporaneously with spray drying, preserves and allows recovery of active clotting factors of rehydrated plasma that has undergone the spray drying process as well as long term stability during storage after drying. As further discussed below, these improvements to certain embodiments of spray drying of blood plasma involving formulation with a SDSAS, also improve the ease and lower the cost of rehydration of the plasma product by allowing the spray dried plasma to be rehydrated with sterile water (e.g., water for injection: WFI).

The present invention contemplates a method of producing spray dried plasma with improved recovery of active plasma proteins and long term stability of plasma proteins. In an embodiment, the method provides for plasma to be dried, the plasma may be selected from citrate phosphate dextrose solution (CPD) plasma or whole blood (WB) plasma. The method further provides for a SDSAS and a spray drying system. The invention further contemplates adjusting the pH of the CPD plasma or WB plasma with the SDSAS by bringing the concentration of the acidic compound to about 0.001 to about 0.050 mmol/mL, which lowers the pH of the plasma to about 5.5 to about 6.5 or to about 7.2 to create formulated plasma.

The present invention further contemplates drying the formulated plasma with the spray drying system to create spray dried formulated plasma, said spray dried formulated plasma having a recovery of active von Willebrand factor (vWF) at least 10 to at least 20 percentage points greater than the recovery of active von Willebrand factor obtained from an otherwise identical spray dried plasma that has not undergone acid formulation with an SDSAS. The SDSAS may be selected from any known in the art, however, citric acid and lactic acid are preferred substances for use in the present invention. The physiologically compatible SDSAS is added to the plasma before spray drying and preferable shortly before spray drying or contemporaneously with spray drying. Additionally, the pH of the plasma may be determined before the addition of a SDSAS to the plasma to determine an appropriate amount of acid to add. In an embodiment, about 7.4 mM of citric acid is added to the CPD plasma or WB plasma. In an embodiment, the pH of the formulated plasma is about 5.5 to about 6.5 or to about 7.2. The present invention further contemplates that the recovery of vWF may be from about 10 to about 20 percentage points to about 40 percentage points greater than the recovery of active von Willebrand factor obtained from an otherwise identical spray dried plasma that has not undergone pretreatment with a SDSAS or about 25 percentage points to about 35 percentage points greater than the recovery of active von Willebrand factor obtained from an otherwise identical spray dried plasma that has not undergone pretreatment with a SDSAS.

The present invention contemplates reconstituting the spray dried formulated plasma of the present invention. The spray dried formulated plasma of the present invention may be reconstituted with any physiologically compatible solution. Further, the spray dried formulated plasma of the present invention may be reconstituted with sterile water (e.g., water for injection (WFI) or similar) or clean, non-sterile water and, if desired, filtered after reconstitution. It is contemplated that the reconstituted spray dried formulated plasma of the present invention has a pH of about 6.8 to about 7.6, or about 6.9 to about 7.5.

In an embodiment, a subject in need of plasma is selected and the reconstituted plasma of the present invention is administered to the subject in need of plasma. Said administration is intravenous.

In an embodiment, it is contemplated that the spray dried formulated plasma is substantially more stable when stored under refrigeration, at ambient temperature or higher temperature, e.g., 37° C., e.g., for two weeks (see, FIGS. 8 and 9) before reconstitution than the spray dried plasma produced from unformulated liquid plasma. It is further contemplated that the stability of the spray dried treated plasma is determined by measuring the activity of von Willebrand factor and/or other plasma proteins.

The present invention contemplates a reconstituted spray dried plasma product for human transfusion (administration), the reconstituted spray dried plasma product having been reconstituted with, for example, sterile water and the reconstituted spray dried plasma product having a pH of about 6.8 to about 7.6 or about 6.9 to 7.5 and comprising active von Willebrand factor of greater than 5 percentage points as compared to the recovery of active von Willebrand factor obtained from an otherwise identical spray dried plasma that has not undergone formulation with a SDSAS; or about 5 percentage points to about 40 percentage points greater than the recovery of active von Willebrand factor obtained from an otherwise identical spray dried plasma that has not undergone pretreatment with a SDSAS. The present invention further contemplates that the active von Willebrand factor is of about 25 percentage points to about 35 percentage points greater than the recovery of active von Willebrand factor obtained from an otherwise identical spray dried plasma that has not undergone formulation with a non-volatile, physiologically compatible acid.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIG. 3 is a schematic illustration detailing embodiments of a collection chamber of the spray dryer assembly of FIGS. 2A-2B.

FIG. 4 (A-C) are: FIG. 4(A) a schematic diagram of spray drying system and possible stress experienced by protein solution and droplet during spray drying. FIG. 4(A) Also shows how contemporaneous dosing may be performed by feeding the SDSAS into the plasma prior to feeding the plasma into the spray dryer. FIG. 4(B) Also shows how contemporaneous dosing may be performed by feeding the SDSAS into the feeding line after the plasma but before the spray dryer.

FIG. 5(A) Cartoon of the vWF A2 domain in its native folded state. FIG. 5(B) The first step of unfolding occurs from the C-terminal end of the vWF A2 domain, influenced by the presence of the vicinal disulphide bond (cysteines depicted by C). Initial unfolding occurs up to, or including, the central b4 sheet in which the scissile bond (YM) is contained. This unfolding intermediate step exposes the high-affinity ADAMTS13 spacer-binding site. FIG. 5(C) Once the stabilizing effect of the calcium-binding site (CBS) is overcome this results in the complete unfolding of the vWF A2 domain and the positioning of the ADAMTS13 active site for nucleophilic attack of the Y1605-M1606 scissile bond

FIG. 14(A) citric acid, FIG. 14(B) lactic acid, and FIG. 14(C) pH.

DETAILED DESCRIPTION

Figure 1A:
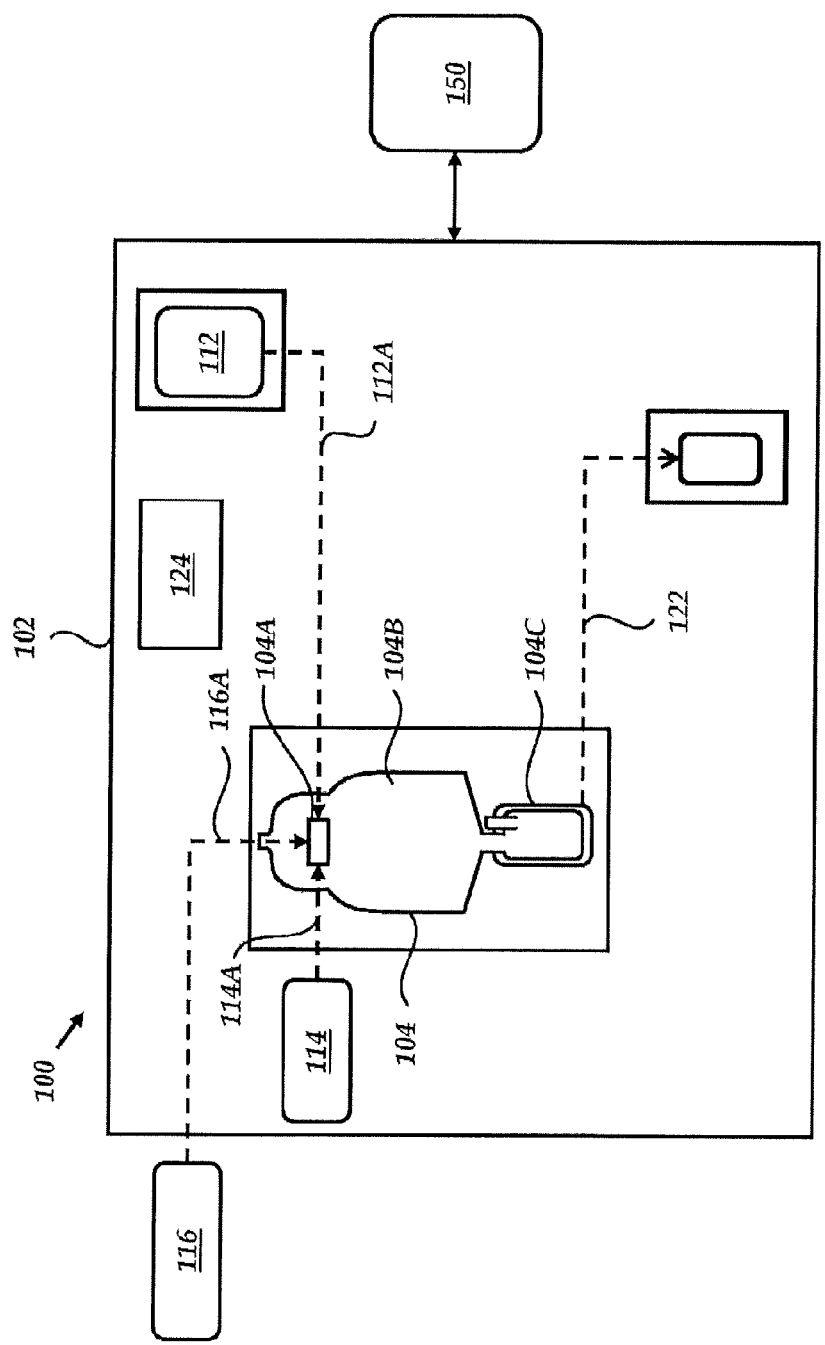
FIG. 1A is a schematic illustration of an embodiment of a spray dryer system of the present disclosure, including a spray dryer device 102 and a spray dryer assembly.

Embodiments of the present disclosure are directed to methods and compositions relating to a spray dried liquid sample. In certain embodiments, the liquid sample is plasma obtained from a blood donor. In a preferred embodiment, the blood donor is human. However, it may be understood that the disclosed embodiments may be employed to spray dry any biological mixture of solid particles and/or molecules in a continuous liquid medium, including, but not limited to, colloids, suspensions and sols (a colloidal suspension of very small particles).

Plasma

Plasma is the fluid that remains after blood has been centrifuged (for example) to remove cellular materials such as red blood cells, white blood cells and platelets. Plasma is generally yellow-colored and clear to opaque. It contains the dissolved constituents of the blood such as proteins (6-8%; e.g., serum albumins, globulins, fibrinogen, etc.), glucose, clotting factors (clotting proteins), electrolytes ($Na^+$, $Ca^{2+}$, $Mg^{2+}$, $HCO_3^-$, $Cl^-$, etc.), hormones, etc. Whole blood (WB) plasma is plasma isolated from whole blood with no added agents except anticoagulant(s). Citrate phosphate dextrose (CPD) plasma, as the name indicates, contains citrate, sodium phosphate and a sugar, usually dextrose, which are added as anticoagulants. The level of citrate in CPD plasma, derived from whole blood, is about 20-30 mM. Thus, the final citrate concentration in the whole blood derived CPD plasma formulated with 7.4 mM citric acid will be about 27.4-37.4 mM.

The plasma of the present invention may be dried after pooling or unit-by-unit. Pooling of multiple plasma units has some benefits. For example, any shortfall in factor recovery on an equal-volume basis can be made up by adding volume from the pool to the finished product. There are negative features as well. Making up volume from the pool to improve factor recovery is expensive. Importantly, pooled plasma must be constantly tested for pathogens as any pathogens entering the pool from, for example, a single donor, runs the risk of harming hundreds or thousands of patients if not detected. Even if detected, pathogen contamination of pooled plasma would render the whole pool valueless. Testing can be obviated by pathogen inactivation of the plasma by irradiation or chemically such as solvent detergent treatment; however, each such treatment adds cost and complexity to pooled plasma processing. In any event, pooled plasma processing is generally unsuitable to the blood centers and generally only really suitable to an industrial, mass production environment.

Conversely, unit-by-unit (unit) collection and processing is well-suited to the blood center environment and eliminates the risk of pooled plasma pathogen contamination by allowing for pre-processing testing for pathogens and tracking of the unit to ensure that each unit leaves the blood center site pathogen free. The inventors have discovered that efficient and effective preservation and recovery of clotting factors is the standard by which successful unit blood plasma processing should be measured. Such efficiency is also very helpful in the pooled plasma environment as well.

Clotting Factors

There are many blood plasma factors associated with clotting. The methods and compositions of the present invention include recovering amounts of active/undenatured fibrinogen, Factor V, Factor VII, Factor IX and vWF from rehydrated plasma that has undergone the spray drying process. Such blood plasma factors are important in patient treatment especially after trauma injuries to promote clotting of wounds. Thus, rapid administration of plasma is an important factor contributing to positive clinical outcomes. The spray dried plasma of the present invention can be readily reconstituted in a few minutes at the location of the trauma event without moving the patient and without time delay. Further, the spray dried plasma of the present invention has high levels of functional proteins that are stable for extended periods of time without refrigeration or freezing.

vWF has generally been difficult to recover and has become one indicator for preservation of all factors. The present invention includes recovering amounts of active/undenatured vWF, in an amount in rehydrated spray dried plasma that is at least about 5 percentage points or greater (e.g., about 5, 10, 15, 20, 25, 30, 35, 40, 45, 50, 60 or greater percentage points) as compared to amounts of active/undenatured vWF of rehydrated spray dried plasma that do not undergo the pre-treatment steps of the present invention. The present invention includes recovering amounts of active/undenatured vWF, in an amount in rehydrated spray dried plasma that is at about 5 percentage points to about 40 percentage points or about 10 percentage points to about 35 percentage points higher as compared to amounts of active/undenatured vWF of rehydrated spray dried plasma that do not undergo the formulation steps of the present invention. vWF activity is typically assayed with an assay called the von Willebrand factor: Ristocetin cofactor [vWF:RCo] assay, as is known to those of skill in the art. The vWF:RCo assay measures the ability of a patient's plasma to agglutinate platelets in the presence of the antibiotic Ristocetin. The rate of Ristocetin induced agglutination is related to the concentration and functional activity of the plasma von Willebrand factor. Another assay, the vWF antigen assay, measures the amount of vWF protein present in a sample.

Spray Dry Stable Acidic Substance (SDSAS)

The present invention contemplates the use of a physiologically compatible spray dry stable acidic substance (SDSAS) as a formulation agent for plasma prior to being spray dried.

While the present invention is not limited by theory, it is presumed by the inventors that the SDSAS of the present invention (e.g., citric acid, lactic acid, etc.) exerts its effects because it prevents or alleviates the rising of the pH of the plasma during the spray drying process. Non-limiting examples of suitable acids are citric acid and lactic acid. Other non-limiting examples of suitable acids are ascorbic acid, gluconic acid and glycine hydrochloride (glycine HCl). Because $CO_2$ is lost from plasma during spray drying, the reaction generating bicarbonate and $H^+$ from $CO_2$ and $H_2O$ is shifted away from $H^+$, thereby increasing the pH (i.e., Chatelier's principle). Citric acid addition (or other SDSAS of the present invention) helps offset this change. Therefore, the plasma is formulated with the SDSAS of the present invention. Because of the formulation step, vWF activity loss is reduced and/or the amount of undenatured vWF is increased, as compared to spray dried plasma not subjected to the formulations steps of the present invention.

Because the physiologically compatible SDSAS of the present invention is included in this manner, the inventors further found out that the rehydration step can be performed by water alone (e.g., WFI). Alternatively, sodium phosphate or other agents can optionally be added to the rehydration solution. Further, any other suitable rehydration fluid as can be determined by one of ordinary skill in the art may be used.

From experiments conducted by the inventors with spray drying, it has been discovered that the von Willebrand factor activity level in plasma dried by spray drying is affected, in part, by the shear forces generated during the aerosolization process (see, Examples, below) and an increase in the pH of the plasma. The present invention shows that the utilization of a step wherein the plasma is formulated with a SDSAS greatly improves the recovery and stability of active vWF over conditions wherein the SDSAS is not used as a formulation agent.

A SDSAS is a substance which does not evaporate easily at room temperature at atmospheric pressure. Typically, the boiling point of the SDSAS will be greater than about 150° C. at atmospheric pressure. Non-volatile acids that are suitable of use as the SDSAS of the present invention include phosphorus-containing acids such as, for example, ortho-phosphoric acid, pyrophosphoric acid, meta-phosphoric acid, poly phosphoric acid, alkyl- and aryl-substituted phosphonic and phosphinic acids, phosphorous acid, and the like, and mixtures thereof. Other non-volatile acids suitable for use as the SDSAS of the present invention include, but are not limited to, ascorbic acid, citric acid, lactic acid, gluconic acid, oxalic acid, halogenated acetic acids, arene sulfonic acids, molybdic acid, phosphotungstic acid, tungstic acid, chromic acid, sulfamic acid, and the like.

SDSAS useful in the process of the invention are capable of replacing the volatile acid, i.e. $CO_2$ that escapes from the plasma during spray drying. As indicated above, examples or suitable acids include, but are not limited to, ascorbic acid, citric acid, gluconic acid, and lactic acid.

A volatile acid as defined herein has a pKa less than about 3 and a boiling point less than about 150° C. at atmospheric pressure. Typically, the pKa of the volatile acid is within the range of about 1 to about 15. Non-limiting examples of volatile acids are hydrogen chloride, hydrogen bromide, hydrogen iodide, hydrogen fluoride, acetic acid, formic acid, hydrogen sulfide, hydrogen selenide, sulfur dioxide, fluorosulfonic acid, methane sulfonic acid, trifluoroacetic acid, trifluoromethanesulfonic acid, and the like.

A volatile strong acid can be fixed with an amino acid or like to render it non-volatile, making it easier to use. For example, volatile hydrogen chloride can be converted to glycine hydrogen chloride (glycine HCl, glycine hydrochloride). Similarly, a corrosive strong acid can be converted to an acidic salt for use in pretreating plasma prior to spray-drying. Examples include $NaHSO_4$ and $NaH_2PO_4$: namely the acidic salts of sulfuric acid.

Non-volatile acids and acidic salts are collectively defined as and included as spray dry stable acidic substance (SDSAS's) in this invention.

In an embodiment, the SDSAS of the present invention is added to the plasma within about 30 minutes, about 20 minutes, about 15 minutes, about 10 minutes, about 5 minutes, about 1 minute or time zero (0 minutes) of spray drying the plasma. In an embodiment, the SDSAS of the present invention is added contemporaneously to the plasma as the plasma is being pumped into the spray drying apparatus. The term "contemporaneously" shall be defined herein as meaning within about 60 seconds, about 50 seconds, about 40 seconds, about 30 seconds, about 20 seconds, about 10 seconds, about 5 seconds, about 1 second and about 0 seconds.

The present inventions relate to adding SDSAS to blood plasma to be spray dried in a time period prior to spray drying short enough to obtain a formulation with the desired pH ("plasma formulation") and to prevent denaturing or damage of certain plasma protein(s) such as von Willebrand's factor due to prolonged exposure to the low pH condition. Keeping the time delay to 30 minutes or less between formulation of the plasma with SDSAS and spray drying, as described below, results in improved recovery of plasma proteins, including von Willebrand factor, without undesirable protein damage due to prolonged exposure to the low pH condition prior to spray drying.

The time period between acid formulation and spray drying will depend on the pH/acidity of the plasma formulation created by the mixing of the SDSAS and the plasma. In an embodiment, the time period between contacting the SDSAS with the blood plasma and spray drying the plasma is in a range between about 0 seconds (e.g., at the time aeroslization occurs: time 0) and about 30 minutes. To minimize protein denaturing, the time between acid formulation of the plasma and spray drying should be kept to minimum. The actual maximum time between formulation and spray drying is determined empirically. This close-in-time formulation at time 0 is referred to herein as "contemporaneous formulation."

Figure 4A:
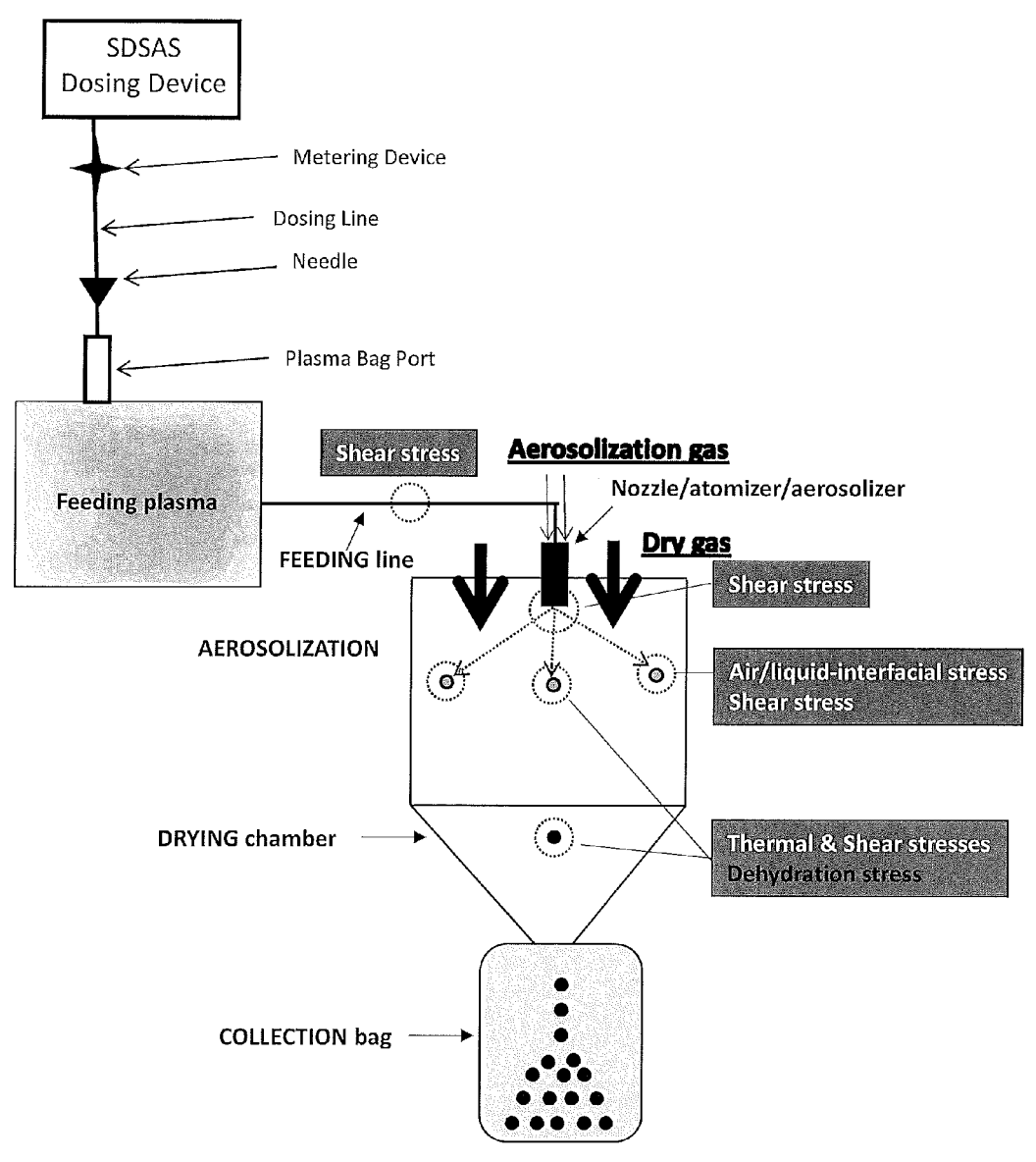

There are a number of methods by which contemporaneous formulation may be carried out. As illustrated in FIG. 4A, in one embodiment a formulation station is provided in association with the spray dryer. In conjunction with the formulation station, the weight or volume of the pre-spray dried plasma is determined and an SDSAS dose measured to obtain the desired pH of the plasma formulation. The SDSAS dose may be introduced into the plasma by any convenient method including by injection through a port on the plasma bag. A formulation station may be manually, semi-automatically or automatically operated. Naturally, the timing of the dosing must be controlled carefully as described above. Timing control may be manual, semi-automatic or automatic.

Figure 4B:
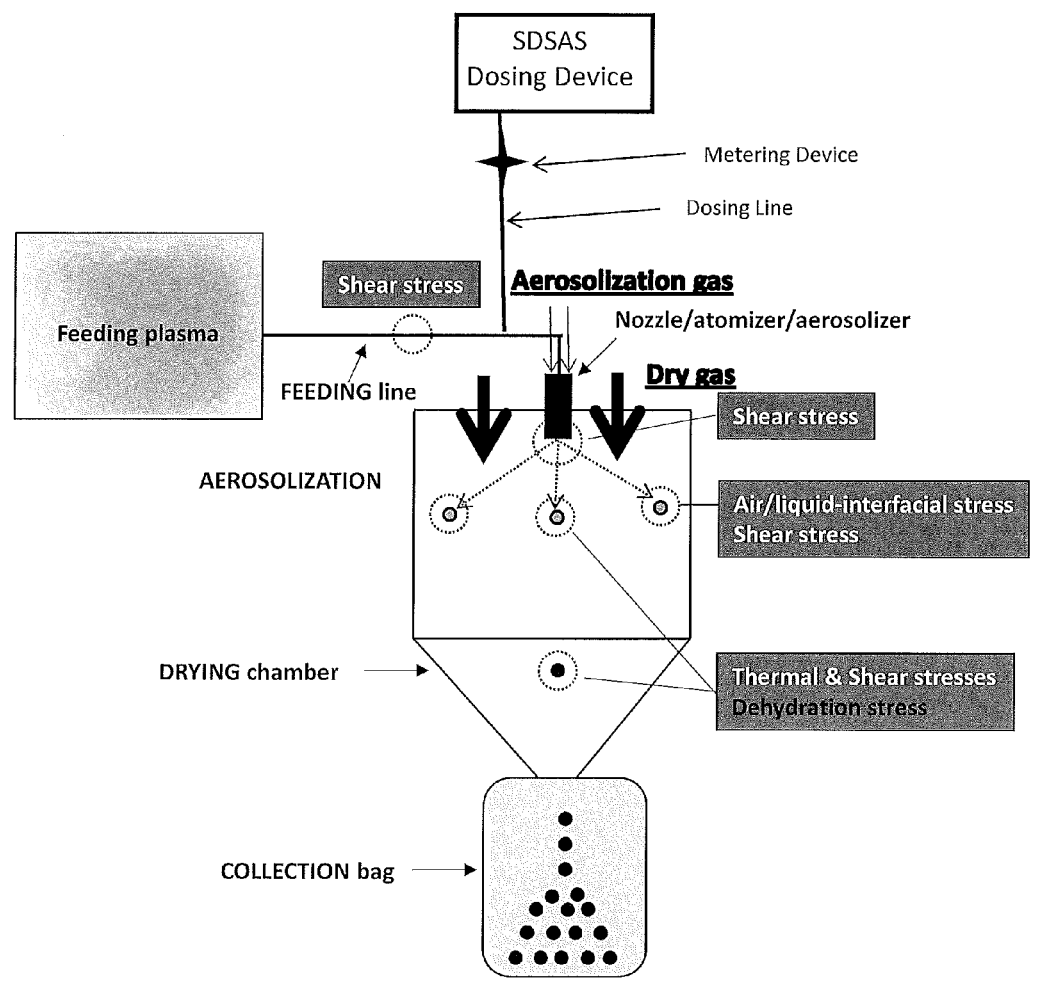

In another embodiment as shown in FIG. 4B, an appropriate dose of SDSAS is introduced into the plasma flow channel of the spray dryer prior to the spray drying head. SDSAS introduction is controlled manually, semi-automatically or automatically to result in the desired plasma formulation.

Figure 4C:
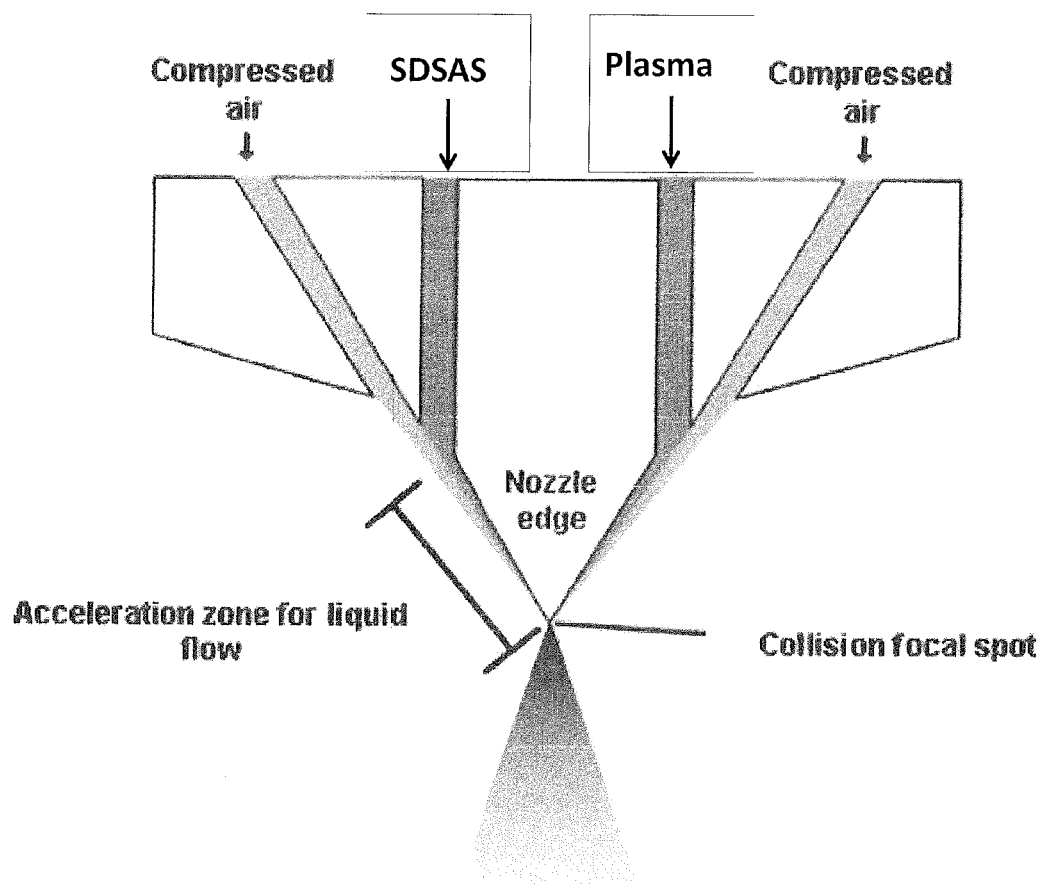
FIG. 4(C) Also shows how contemporaneous dosing may be performed by feeding both the plasma and the SDSAS into the spray head simultaneously.

In a further embodiment shown in FIG. 4C, an appropriate dose of SDSAS is introduced into the spray drying chamber sufficiently close to the spray drying nozzle so that the SDSAS and plasma are mixed together to form a plasma formulation before spray drying occurs in the spray drying chamber connected to the spray drying head. SDSAS introduction is controlled manually, semi-automatically or automatically to result in the desired plasma formulation.

Protein Stability

Proteins potentially undergo physical degradation (e.g., unfolding, aggregation, insoluble particulate formation) by a number of mechanisms. Many proteins are structurally unstable in solution and are susceptible to conformational changes due to various stresses encountered during purification, processing and storage. These stresses include temperature shift, exposure to pH changes and extreme pH, shear stress, surface adsorption/interface stress, and so on. Proteins in solutions can be converted to solid formats (i.e., converted to a powder or other dry format by having the water and other volatile components of the protein solution greatly reduced or removed) for improved storage using a number of methods.

Freeze drying (also known as lyophilization) is the most common processing method for removing moisture from biopharmaceuticals, and can increase the stability, temperature tolerance, and shelf life of these products. It is a process wherein a suspension, colloid or solid is frozen and then "dried" under a vacuum by sublimation (phase transition). In this process, proteins can suffer from cold denaturation, interface stress [adsorption at the water/ice-interface], exposure to increasing alkaline pH ($CO_2$ loss), and dehydration stress. Freeze drying is well established within the industry. However, it requires expensive equipment that takes up a great deal of space within a production facility. Freeze drying also can take days to complete, and manufacturers that need a powdered product must incorporate a granulation step to the process. In an environment where budgets are tightening, and where time and facility space are at a premium, freeze drying might be a difficult option for some companies. Because of the space needed, drying plasma by freeze-drying technology is limited to plasma manufacturers, and cannot be implemented in blood centers.

Because of the difficulties inherent with freeze drying of plasma with regard to time, space and cost, the present invention is directed towards an improved spray drying process for plasma that overcomes the known difficulties related to the spray drying of plasma.

In the spray-drying process, the viscous liquid is pumped through the feeding line to the nozzle, where the exiting fluid stream is shattered into numerous droplets under aerosol gas. The liquid droplets are met with dry gas and turned into dry particles. It is a much shorter and less expensive process than the freeze drying process, allowing it to be implemented in research labs and blood centers. However, in this process, plasma proteins can suffer from extensive shear stress, interface stress, thermal stress, dehydration stress and exposure to extreme pH (see, FIG. 4A).

Aerosolization exposes the liquid sample to shear stress and produces an extremely rapid and very large expansion of the air-liquid interface. The syngerstic effects of shear stress and air-liquid interfacial stress can cause severe detrimental effects on labile compounds such as proteins. Complex biological molecules are difficult to spray dry because they are very sensitive to high shear stress. Although some control relating to the amount of shear stress encountered can be obtained by, for example, choice of the type of atomizer used and the aerosolization pressure used, it is very challenging to apply spray drying technology to human plasma because it contains so many diverse proteins. The diverse proteins may be susceptible to different stresses and this can make it difficult determine processing conditions suitable for all of the types of proteins found in plasma. In particular, vWF, which is designed by nature to be shear sensitive for its biological functions, is the most shear-force sensitive human plasma protein. Most of the other plasma proteins remain largely intact after spray drying except vWF. As shown in the Examples section, spray-drying diminished vWF activity to below the level of detection (see, Example 1, FIG. 6).

Ionizable amino acid residues have been shown to play important roles in the binding of proteins to other molecules and in enzyme mechanisms. They also have a large influence on protein structure, stability and solubility. The types of interactions these side chains will have with their environment depend on their protonation state. Because of this, their pKa values and the factors that influence them are a subject of intense biochemical interest. Strongly altered pKa values are often seen in the active sites of enzymes, to enhance the ability of ionizable residues to act as nucleophiles, electrophiles or general bases and acids. As a consequence of the change in protonation of these residues, the stability of proteins is pH-dependent. Therefore, we rationalized that inhibition of the alkalination of plasma during spray drying can potentially improve the processing and storage stabilities of many plasma proteins.

U.S. Pat. No. 8,518,452 (the '452 patent) to Bjornstrup, et al., teaches the use of citric acid as a pretreatment for lyophilized plasma.

As mentioned above, the spray drying process subjects plasma proteins to different forces than are found in the lyophilization process. First, spray drying exposes plasma proteins to high stress forces during the aerolization process as the plasma is forced through the narrow orifice exposed to high rate of air flow that is necessary to create suitably sized droplets for drying. Second, the spray drying process exposes plasma proteins to high temperatures that are necessary to force the water from the aerosolized droplets. Third, the spray drying process subjects the plasma proteins to dramatic and rapid increases in pH as a result of the rapid release of $CO_2$ during drying. Since lyophilization does not subject plasma proteins to these forces, and especially to this unique combination of forces, one of ordinary skill in the art would not look to nor find suggestion or motivation in the lyophilization art with regard to improving the spray drying process for plasma.

Indeed, U.S. Pat. No. 7,931,919 (the '919 patent) to Bakaltcheva, et al. teaches the use of 2 mM citric acid in lyophilized plasma. However, citric acid merely acted as a pH adjuster, did not provide any benefits for improving quality of product during acquirement or storage.

The present invention provides for the high recovery rate of vWF and for storage stability of active plasma proteins; a goal that has eluded those of skill in the art of drying plasma. In fact, the '452 patent discussed above provides no teaching of either recovery or long term stability of active plasma protein function with regard to the disclosed lyophilization process. Further, any specific teaching with regard to the recovery and stability of vWF is missing from the '452 patent. vWF has been notoriously difficult to recover after the drying of plasma. This lack of teaching in the '452 patent is likely indicative of the failure of the methods disclosed in the '452 patent with regard to successfully recovering active vWF.

U.S. Pat. No. 7,297,716 (the '716 patent) to Shanbrom teaches the use of 2% by weight of citric acid and its salts to reduce bacterial growth and adjust/maintain pH in cryoprecipitates of blood and plasma for enhancing their purity and safety. The '716 patent, like the '452 patent provides no teaching of recovered plasma protein activity and stability. While the '716 patent mentions that citrate appears to stabilize labile proteins against heat denaturation, it provides no support for the statement and provides no teaching with regard to actual recovered protein activity or long term stability of recovered proteins, especially vWF.

Thus, the present inventors, in spite of the difficulties associated with the spray drying of plasma as known to those of skill in the art, have achieved a spray drying process for plasma that results in high recovery and high stability of plasma proteins, especially, but not limited to vWF, wherein the recovery of vWF is in an amount in rehydrated spray dried plasma that is at least about 5 percentage points or greater (e.g., about 5, 10, 20, 30, 40, 50, 60, 70, 80 percentage points or greater) as compared to amounts of active/undenatured vWF of rehydrated spray dried plasma that does not undergo the pretreatment steps of the present invention.

The compositions and steps of the present invention relate to the impact of the formulation of liquid plasma with a SDSAS, for example, citric acid (CA) on the recovery from the spray drying process and stability (during storage of dried and rehydrated plasma after spray drying) of vWF and other coagulation factors. This can be done by adding a SDSAS such as, for example, citric acid or lactic acid to the liquid plasma before spray drying begins or contemporaneously with the spray drying process. During the spray drying process, $CO_2$ loss occurs which causes the pH of the plasma composition to become more alkaline (e.g., to increase) and adding SDSAS thereby maintains the plasma pH in a range to prevent significant denaturing of the clotting factors, esp. vWF. Thus, the pretreatment of plasma with citric acid, or other SDSAS, serves at least three main purposes: 1) increases in-process recovery of plasma proteins; 2) increases stability of plasma proteins during storage; and 3) allows spray dried plasma to be rehydrated with water (e.g., sterile water, WFI), eliminating the need for a specific rehydration solution.

When liquid plasma is formulated with SDSAS before it is dried, the acid resides in the dried plasma product at a level consistent to improved storage lifetime and reduced degradation of clotting factors during storage. A "level consistent to improve storage lifetime" also means, herein, at a level that results in a physiological pH upon reconstitution of the spray dried plasma. The use of the SDSAS also permits simple rehydration by low cost, readily available water for injection or, in an emergency, plain water at a physiological pH. The convenience, lowered cost and improved safety associated with direct rehydration by water is evident. Advantages include savings in being able to ship dried plasma product without the weight and bulk of rehydration fluid and savings in the cost from not having to specially formulate rehydration fluid and reduction or elimination of refrigeration or freezing during storage.

Thus, the inventors have discovered that plasma formulation by a SDSAS results in spray dried plasma that has very high recovery of plasma proteins, especially vWF, highly improved storage properties of the dried plasma and approximately neutral pH when rehydrated with water without a buffering rehydration fluid. Thus, the present invention permits spray dried plasma to be manufactured without the additional expense and complexity of pretreatment with additional stabilizers such as polyols and others known in the art. However, the use of stabilizers is not contraindicated and may be beneficial in some instances.

In a further embodiment, a new composition of matter for blood plasma spray drying is created by dosing by any means the blood plasma prior to spray drying with added citrate (i.e., citric acid) or other suitable SDSAS at an appropriate concentration, as disclosed herein.

In a further embodiment the newly dosed citrate formulated blood plasma before spray drying has a concentration of citrate of about 27.5 mM and about 40.4 mM, or of about 31.6 mM and 34.2 mM.

In a further embodiment a new spray dried blood plasma product is created by spray drying blood plasma formulated with an appropriate level of a suitable SDSAS (e.g., citric acid) prior to or contemporaneously with drying and then drying the blood plasma to the desired level of moisture. The desired level of moisture is generally between 2%-10%, 3%-8% and 4%-6%

In various embodiments, citric acid or other SDSAS is added to the plasma as a formulation. Experiments relating to the effect of citric acid or other SDSAS on protection of the activities of proteins found in plasma are explained further in the exemplification section of this specification. The concentrations at which citric acid, for example, is used are between about 1 to about 15 mM, or between about 5 mM to about 10 mM (e.g., 7.4 mM). Accordingly, plasma proteins can be preserved better when citric acid, at the indicated concentrations, is added to it prior to or contemporaneously with spray drying. The activity of vWF is provided in the exemplification because this factor is especially sensitive to denaturing and damage by spray drying (See, FIG. 6 and FIG. 7) and, thus, is a good indicator protein to show the beneficial effects of citric acid or other SDSAS with regard to recovery and stability of the spray dried plasma proteins. Examples of other physiologically compatible SDSAS are known to those of ordinary skill in the art and described herein.

Spray Dryer and the Spray Drying Process

In general, a spray dryer system (spray dryer device) is provided for spray drying a liquid sample such as blood plasma. In an embodiment, the spray dryer system of the present disclosure includes a spray dryer device and a spray dryer assembly. The spray dryer device is adapted, in an aspect, to receive flows of an aerosolizing gas, a drying gas, and plasma liquid from respective sources and coupled with the spray dryer assembly. The spray dryer device may further transmit the received aerosolizing gas, drying gas, and plasma to the spray dryer assembly. Spray drying of the plasma is performed in the spray dryer assembly under the control of the spray dryer device. Any suitable spray drying system may be used in the present invention. For exemplification, a suitable spray dryer is described below.

In certain embodiments, the spray dryer assembly includes a sterile, hermetically sealed enclosure body and a frame to which the enclosure body is attached. The frame defines first, second, and third portions of the assembly, separated by respective transition zones. A drying gas inlet provided within the first portion of the assembly, adjacent to a first end of the enclosure body.

A spray drying head is further attached to the frame within the transition zone between the first and second portions of the assembly. This position also lies within the incipient flow path of the drying gas within the assembly. During spray drying, the spray drying head receives flows of an aerosolizing gas and plasma and aerosolizes the plasma with the aerosolizing gas to form an aerosolized plasma. Drying gas additionally passes through the spray drying head to mix with the aerosolized plasma within the second portion of the assembly for drying. In the second portion of the assembly, which functions as a drying chamber, contact between the aerosolized plasma and the drying gas causes moisture to move from the aerosolized plasma to the drying gas, producing dried plasma and humid drying gas.

In alternative embodiments, the aerosolizing gas may be omitted and the spray dryer assembly head may include an aerosolizer that receives and atomizes the flow of plasma. Examples of the aerosolizer may include, but are not limited to, ultrasonic atomizing transducers, ultrasonic humidified transducers, and piezo-ultrasonic atomizers. Beneficially, such a configuration eliminates the need for an aerosolizing gas, simplifying the design of the spray dryer device and assembly and lowering the cost of the spray dryer system.

The spray drying head in an embodiment is adapted to direct the flow of drying gas within the drying chamber. For example, the spray drying head includes openings separated by fins which receive the flow of drying gas from the drying gas inlet. The orientation of the fins allows the drying gas to be directed in selected flow pathways (e.g., helical). Beneficially, by controlling the flow pathway of the drying gas, the path length over which the drying gas and aerosolized blood plasma are in contact within the drying chamber is increased, reducing the time to dry the plasma.

The dried plasma and humid drying gas subsequently flow into the third portion of assembly, which houses a collection chamber. In the collection chamber, the dried plasma is isolated from the humid drying gas and collected using a filter. For example, the filter in an embodiment is open on one side to receive the flow of humid air and dried plasma and closed on the remaining sides. The humid drying gas passes through the filter and is exhausted from the spray dryer assembly.

In alternative embodiments, the filter is adapted to separate the collection chamber into two parts. The first part of the collection chamber is contiguous with the drying chamber and receives the flow of humid drying gas and dried plasma. The dried plasma is collected in this first part of the collection chamber, while the humid air passes through the filter and is exhausted from the spray dryer assembly via an exhaust in fluid communication with the second part of the spray dryer assembly.

After collecting the dried plasma, the collection chamber is separated from the spray dryer assembly and hermetically sealed. In this manner, the sealed collection chamber is used to store the dried plasma until use. The collection chamber includes a plurality of ports allowing addition of water to the collection chamber for reconstitution of the blood plasma and removal of the reconstituted blood plasma for use. The collection chamber may further be attached to a sealed vessel containing water for reconstitution.

When handling transfusion products such as blood plasma, the transfusion products must not be exposed to any contaminants during collection, storage, and transfusion. Accordingly, the spray dryer assembly, in an embodiment, is adapted for reversible coupling with the spray dryer device. For example, the spray dryer assembly is coupled to the spray dryer device at about the drying gas inlet. Beneficially, so configured, the spray dryer assembly accommodates repeated or single use. For example, in one embodiment, the spray dryer assembly and spray drying head is formed from autoclavable materials (e.g., antibacterial steels, antibacterial alloys, etc.) that are sterilized prior to each spray drying operation. In an alternative embodiment, the spray dryer head and spray drying chamber is formed from disposable materials (e.g., polymers) that are autoclaved prior to each spray drying operation and disposed of after each spray drying operation.

Reference will now be made to FIG. 1A, which schematically illustrates one embodiment of a spray dryer system 100. The system 100 includes a spray dryer device 102 configured to receive a spray dryer assembly 104. A source of plasma 112, a source of aerosolizing gas 114, and a source of drying gas 116 are further in fluid communication with the spray dryer assembly 104. During spray drying operations, a flow of the drying gas 116A is drawn within the body of the assembly 104. Concurrently, a flow of a blood plasma 112A and a flow of aerosolizing gas 114A are each drawn at selected, respective rates, to a spray drying head 104A of the assembly 104. In the spray dryer assembly 104, the flow of blood plasma 112A is aerosolized in the spray dryer head 104A and dried in a drying chamber 104B, producing a dried plasma that is collected and stored for future use in a collection chamber 104C. Waste water 122 removed from the blood plasma during the drying process is further collected for appropriate disposal.

The spray dryer device 102 further includes a spray dryer computing device 124. The spray dryer computing device 124 is adapted to monitor and control a plurality of process parameters of the spray drying operation. The spray dryer computing device 124 further includes a plurality of user interfaces. For example, one user interface may allow an operator to input data (e.g. operator information, liquid sample information, dried sample information, etc.), command functions (e.g., start, stop, etc.). Another user interface may display status information regarding components of the spray drier device (e.g., operating normally, replace, etc.) and/or spray drying process information (e.g., ready, in-process, completed, error, etc.).

The spray dryer device 102 is in further communication with a Middleware controller 150. The spray dryer device 102 records one or more parameters associated with a spray drying operation. Examples of these parameters includes, but are not limited to, bibliographic information regarding the blood plasma which is spray dried (e.g., lot number, collection date, volume, etc.), bibliographic information regarding the spray drying operation (e.g., operator, date of spray drying, serial number of the spray dryer assembly 104, volume of dried plasma, etc.), process parameters (e.g., flow rates, temperatures, etc.). Upon completion of a spray drying operation, the spray dryer device 102 communicates with the middleware controller to transmit a selected portion or all the collected information to the middleware controller 150.

For example, a spray drying system 100 may be housed in a blood bank facility. The blood back facility receives regular blood donations for storage. Liquid plasma is separated from whole blood donations, dried using the spray drying system 100 and subsequently stored until use. The middleware controller 150 comprises one or more computing devices maintained by the blood bank for tracking stored, dried blood. Beneficially, by providing a spray drying system 100 capable of relaying information regarding dried plasma to a middleware controller 150 of the blood center in which it is housed, information regarding the stored blood is then automatically conveyed to the blood center.

Figure 1B:
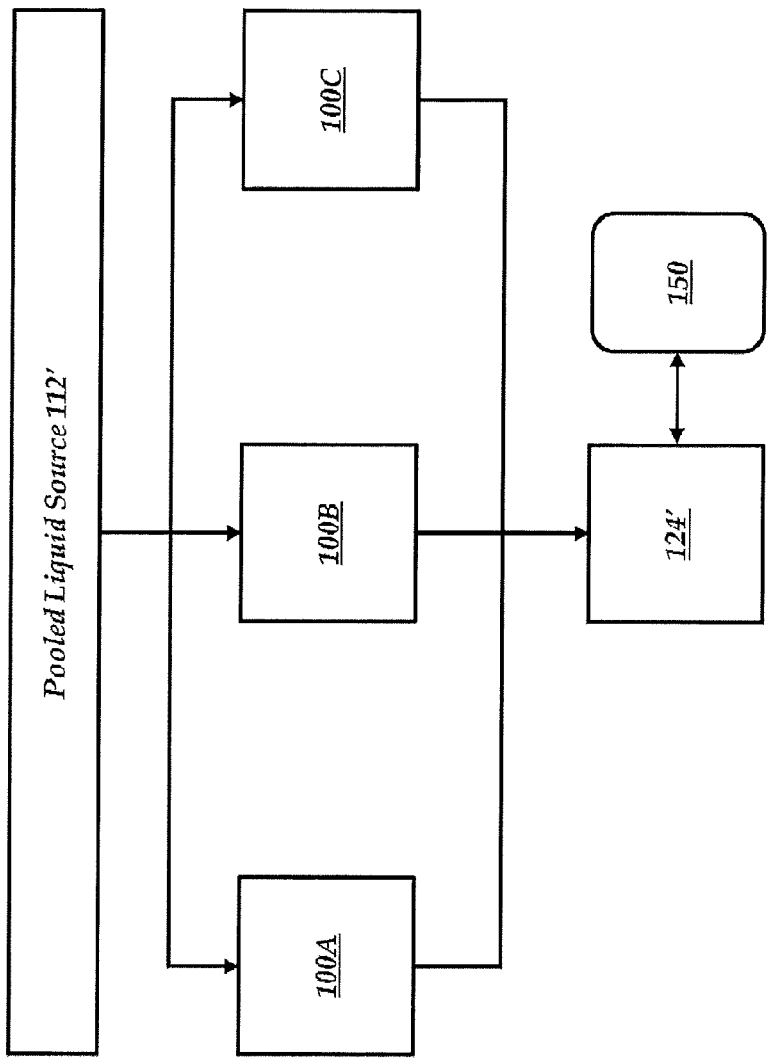
FIG. 1B is a schematic illustration of a plurality of the spray dryer systems of FIG. 1A for use with a pooled liquid source.

In an alternative embodiment, illustrated in FIG. 1B, a plurality of spray dryer systems 100A, 100B, . . . 100N can be used in combination with a pooled plasma source 112'. In general, the pooled plasma source 112' is a bulk source of blood plasma having a volume larger than one blood unit, as known in the art (e.g., approximately 1 pint or 450 mL). Two or more of the spray dryer systems 100A, 100B . . . 100N can operate concurrently, each drawing blood for spray drying from the pooled plasma source 112', rather than a smaller, local blood source.

The spray dryer systems 100A, 100B . . . 100N in a pooled environment can operate under the control of a computing device 124'. The computing device 124' is similar to computing device 124 discussed above, but adapted for concurrent control of each of the spray dryer systems 100A, 100B . . . 100N. The spray dryer computing device 124' further communicates with a remote computing device 150, as also discussed above.

The use of a pooled plasma source 112', provides advantages over a smaller, local plasma source, such as plasma source 112. When pooled prior to drying, the pooled liquid plasma can be formulated for pathogen inactivation with UV light, a chemical, and the like. The pooled liquid plasma is dried using one or more spray drying systems 100 of the present invention and then the dried plasma can be collect in a single collection chamber or a plurality of collection chambers. If the pooled plasma is dried for human transfusion, then each collection container can be configured with an attached rehydration solution. If the pooled plasma is to be used for fractionation purposes, then it is collected in a configured without the rehydration solution. Further embodiments of a spray dryer device 102 for use with the disclosed spray dryer assembly 104 may be found in U.S. patent application Ser. No. 13/952,541, filed on Jul. 26, 2013 and entitled "Automated Spray dryer," the entirety of which is hereby incorporated by reference.

Figure 2A:
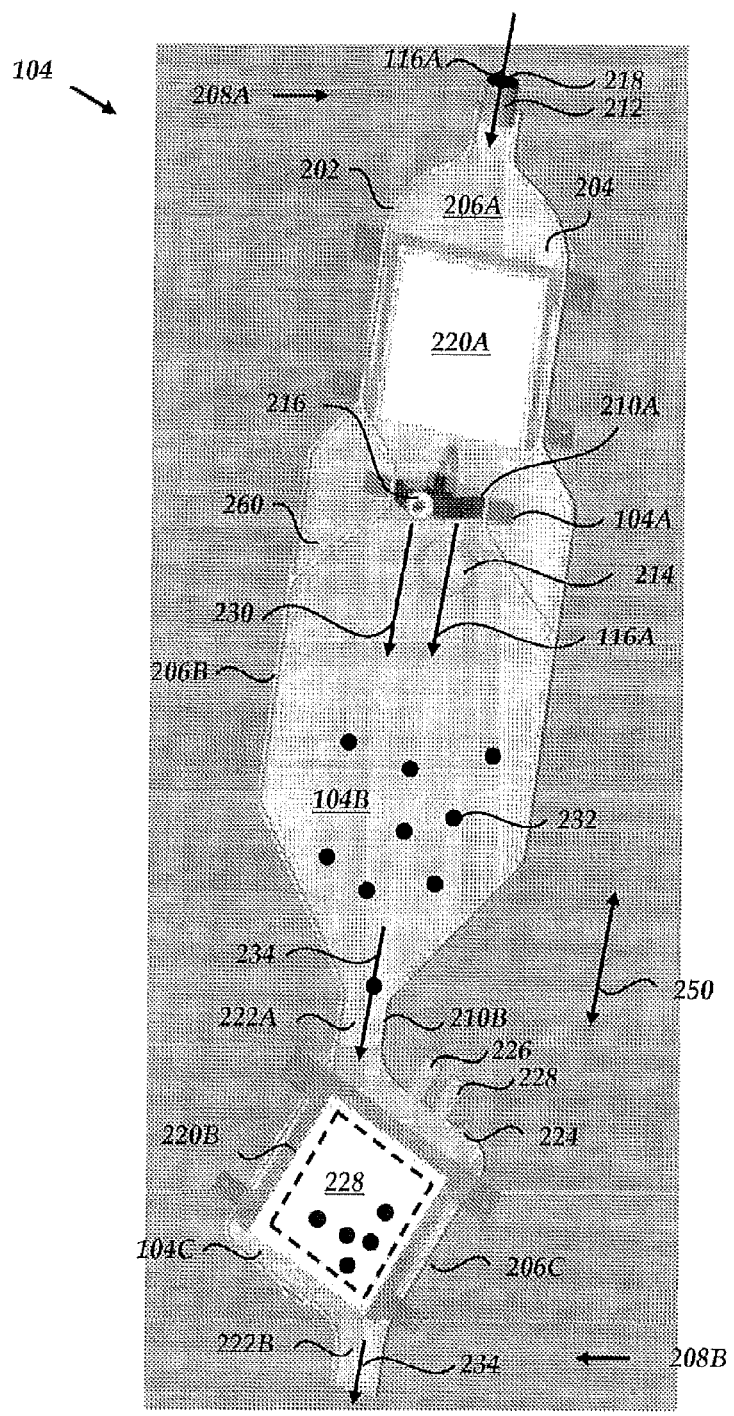
FIGS. 2A and 2B are schematic illustrations of the spray dryer assembly of FIG. 1A.
Figure 2B:
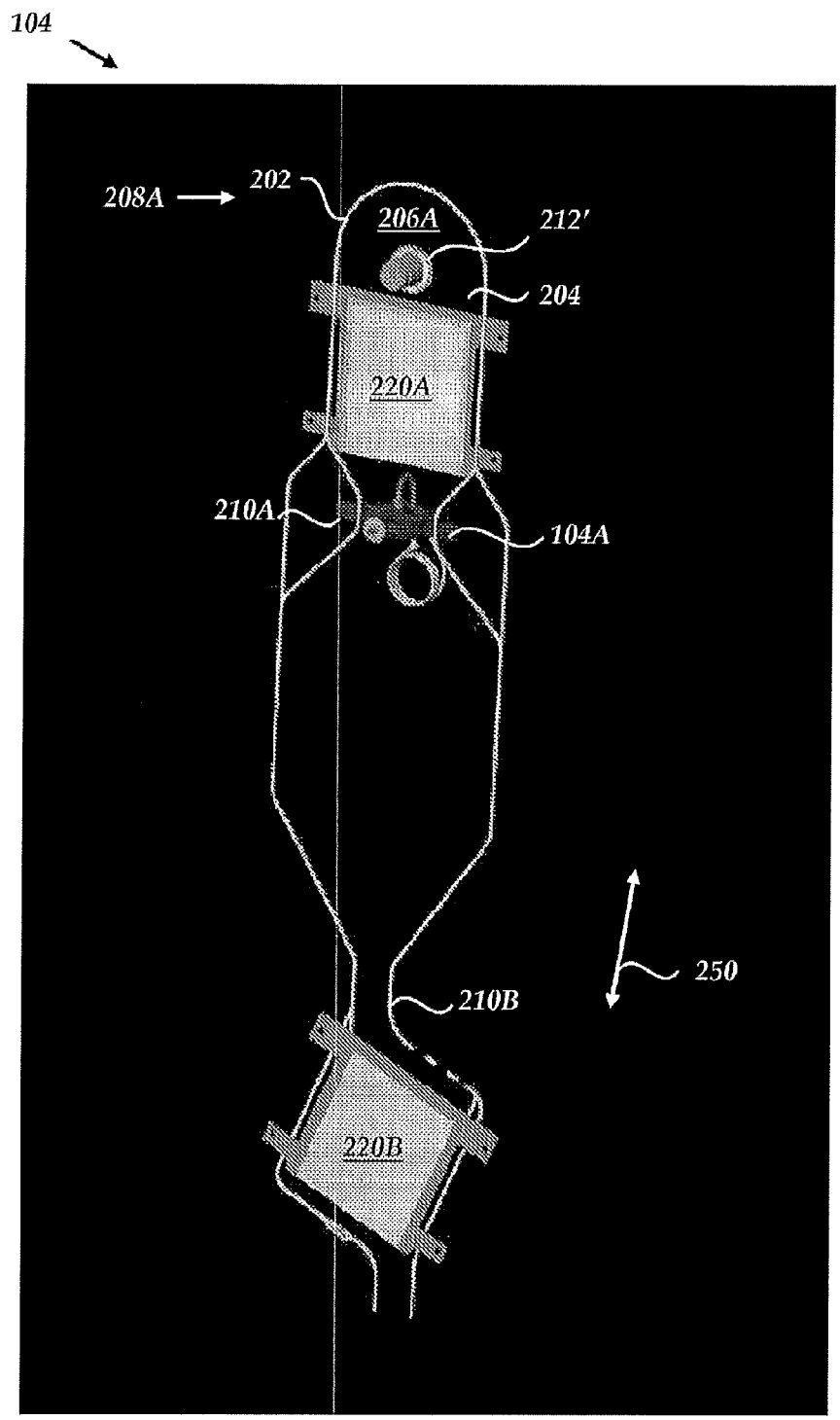

FIGS. 2A and 2B illustrate embodiments of the spray dryer assembly 104 in greater detail. As illustrated in FIG. 2A, the spray dryer assembly 104 includes a frame 202. An enclosure or body 204 having first and second ends 208A, 208B further extends about and encloses the frame 202. Thus, the body 204 adopts the shape of the frame 202. The enclosure 204 may further include a dual layer of film sealed together about the periphery of the frame 202.

In certain embodiments, the frame 202 may define a first portion 206A, a second portion 206B, and a third portion 206C of the assembly 104. The first portion of the assembly 206A is positioned adjacent the first end 208A of the body 204. The third portion of the assembly 206C is positioned adjacent to the second end 208B of the enclosure 204. The second portion of the assembly 206B is interposed between the first and third portions of the assembly 206A, 206C.

The frame 202 further defines first and second transition zones 210A, 210B between the first, second, and third portions of the assembly 206A, 206B, 206C. For example, the first transition zone 210A may be positioned between the first and second portions of the assembly 206A, 206B and the second transition zone 210B may be positioned between the second and third portions of the assembly 206B, 206C. In certain embodiments, the frame 202 may narrow in width, as compared to the width of the surrounding assembly within the transition zones 210A, and/or 210B. The relatively narrow transition zones 210A, 210B help to direct the flow of drying gas 116A through the assembly 104.

In further embodiments, the body 204 may include a drying gas inlet 212, adjacent to the first end 208A. The drying gas inlet 212 may be adapted to couple with the spray dryer device 102 to form a hermetic and sterile connection that allows the flow of drying gas 116A to enter the assembly 104. In one embodiment, illustrated in FIG. 2A, the drying gas inlet 212 is positioned within the first portion of the assembly 206A, at about the terminus of the first end of the body 208A. In this configuration, the flow of drying gas 116A is received within the assembly 104 in a direction approximately parallel to a long axis 250 of the assembly 104.

In an alternative embodiment of the spray dryer assembly 104, illustrated in FIG. 2B, the body 204 may include a drying gas inlet 212'. The position of the drying gas inlet 212' is moved with respect to drying gas inlet 212. For example, the drying gas inlet 212' may be positioned within the first portion of the assembly 206A and spaced a selected distance from the terminus of the first end of the enclosure 208A. In this configuration, the flow of drying gas 116A may be received within the assembly 104 in a direction that is not parallel to the long axis 250 of the assembly 104. For example, in a non-limiting embodiment, the flow of drying gas 116A is received within the assembly 104 in a direction that is approximately perpendicular to the long axis 250 of the assembly 104.

In certain embodiments, the spray dryer assembly 104 may further include a removable cover 218. The cover 218 may be employed prior to coupling of the spray dryer assembly 104 with the spray drier device 102 in order to inhibit contaminants from entering the spray dryer assembly. In certain embodiments, the cover 218 may be removed immediately prior to coupling with the spray dryer device 102 or frangible and penetrated by the spray dryer device 102 during coupling with the spray dryer assembly 104.

The drying gas 116A received by the assembly 104 is urged to travel from the first portion 206A, through the second portion 206B, to the third portion 206C, where it is removed from the assembly 104. As the drying gas 116A travels within the first portion of the assembly 206A towards the second portion of the assembly 206B, the drying gas 116A passes through a first filter 220A which filters the drying gas 116A entering the assembly 104 in addition to any filtering taking place within the spray dryer device 102 between the drying gas source 116 and the drying gas inlet 212. In certain embodiments, the first filter 220A is a 0.2 micron filter having a minimum BFE (bacterial filter efficiency) of $10^6$. The filter 220A further helps to ensure the cleanliness of the flow of drying gas 116A.

In an embodiment, during primary drying, the flow of drying gas BFE received by the spray drier assembly BFE may possess a temperature between about 50° C. and about 150° C. and a flow rate of between about 15 CFM to about 35 CFM. The flow of aerosolizing gas 116A can possess a flow rate of between about 5 L/min and about 20 L/min and a temperature between about 15° C. to about 30° C. (e.g., 24° C.). The flow of liquid sample 112A may possess a flow rate of between about 3 ml/min to about 20 ml/min. As the plasma is dried, the flow of the aerosolizing gas 114A, the flow of drying gas 116C, or both may direct the flow of the dried sample 232 through at least a portion of the spray dryer assembly 104 (e.g., the drying chamber, the collection chamber or both).

In an embodiment, the assembly 104 may further include a spray drying head 104A, a drying chamber 104B, and a collection chamber 104C in fluid communication with one another. The spray drying head 104A may be mounted to the frame 202 and positioned within the first transition zone 210A. So positioned, the spray drying head 104A is also positioned within the flow of drying gas 116A traveling from the first portion of the assembly 206A to the second portion of the assembly 206B. The spray drying head 104A may be further adapted to receive the flow of plasma 112A and the flow of aerosolizing gas 114A through respective feed lines 214, 216 and output aerosolized plasma 230 to the drying chamber 104B.

In further embodiments, the drying chamber 104B and collection chamber 104C may be positioned within the second and third portions of the assembly 206B, 206C, respectively. The drying chamber 104B inflates under the pressure of the flow of drying gas 116A and provides space for the aerosolized blood plasma 230 and the flow of drying gas 116A to contact one another. Within the drying chamber 104B, moisture is transferred from the aerosolized blood plasma 230 to the drying gas 116A, where the drying gas 116A becomes humid drying gas 234. The aerosolized flow of blood plasma 230 and the flow of drying gas 116A are further separated, within the drying chamber 104B, into dried plasma 232 and humid drying gas 234. In certain embodiments, the dried plasma 232 may possess a mean diameter of less than or equal to 25 μm.

The humid drying gas 234 and dried plasma 232 are further drawn into the collection chamber 104C through an inlet port 222A of the collection chamber 104C, positioned within the second transition zone 210B, connecting the collection chamber 104C and the drying chamber 104B. The collection chamber 104 includes a second filter 220B which allows through-passage of the humid drying gas 234 and inhibits through-passage of the dried plasma 232. As a result, the humid drying gas 234 passing through the filter 220B is separated from the dried plasma 232 and exhausted from the collection bag 104C through an exhaust port 222B of the collection chamber 104C that forms the second end 208B of the body 204. For example, a vacuum source (e.g., a vacuum pump) may be in fluid communication with the exhaust port 222B of the collection chamber 104C to urge the humid drying gas 234 through exhaust port b. Concurrently, the dried plasma 232 is retained in a reservoir 228 of the collection chamber 104C. The collection chamber 104C is subsequently hermetically sealed at about the inlet and exhaust ports 222A, 222B, and detached (e.g., cut) from the spray dryer assembly 104, allowing the collection chamber 104C to subsequently function as a storage vessel for the dried plasma 232 until use.

With reference to FIG. 3, the collection chamber 104C further includes a plurality of one-way valves 702A, 702B positioned at about the inlet port 222A and the exhaust port 222B, respectively. The one-way valve 702A may function to permit gas flow from the drying chamber 104B to the collection chamber 104C and inhibit gas flow from the collection chamber 104C to the drying chamber 104B. The one-way valve 702B may function to permit gas flow from the collection chamber 104C while inhibiting gas flow into the collection chamber 104C via the exhaust port 222B.

The collection chamber 104C may be further configured for use in rehydrating the dried plasma 232. For example, the collection chamber 104C may include a rehydration port 224, a plurality of spike ports 226, and a vent port 228. The rehydration port 224 may be used to communicate with a source of rehydration solution, allowing the rehydration solution to come in contact with the dried plasma 232 within the collection chamber 104C to form reconstituted plasma. The reconstituted plasma may be subsequently drawn from the collection chamber 104C through the spike ports 226.

The discussion will now turn to further embodiments of spray drying processes which include secondary plasma drying operations, as discussed in U.S. patent application Ser. No. 14/670,127, which is incorporated herein by reference. In brief, it has been recognized that high levels of residual moisture in stored, dried plasma (e.g., moisture contents above about 3% to about 10%, as compared to the moisture content of the liquid plasma) reduce the shelf life of the dried plasma. However, given the relatively low moisture content of the dried plasma collected within the collection chamber, exposure of this collected, dried plasma to elevated temperatures may result in damage to one or more the plasma proteins, rendering the dried plasma unsuitable for later reconstitution and use. Accordingly, embodiments of secondary drying operations discussed herein are designed to complement the primary spray drying processes discussed above, allowing for further reduction in the moisture content of the plasma after primary drying is completed, without significantly damaging the plasma proteins. As a result, the dried plasma stored after undergoing primary and secondary drying possesses an improved shelf life, while remaining suitable for later reconstitution and use. It has been identified that embodiments of the secondary drying processes discussed in U.S. patent application Ser. No. 14/670,127 may be employed to produce dried plasmas having less than or equal to about 3% moisture content, as compared to the liquid plasma, without significant damage to the plasma proteins, when performed at temperatures of less than or equal to about 70° C. Such secondary drying procedures are compatible with the invention of the present application.

The entire teachings of the all applications, patents and references cited herein are incorporated herein by reference. Specifically, U.S. Pat. Nos. 7,993,310, 8,469,202, 8,533, 971, 8,407,912, 8,595,950, 8,601,712, 8,533,972, 8,434,242, US Patent Publication Nos. 2010/0108183, 2011/0142885, 2013/0000774, 2013/0126101, 2014/0083627, 2014/0083628, 2014/0088768, and U.S. patent application Ser. No. 14/670,127 are incorporated herein by reference and ae instructive of what one of ordinary skill in the art would know and understand at the time of the present invention.

Ranges of values include all values not specifically mentioned. For example, a range of "20% or greater" includes all values from 20% to 100% including 35%, 41.6%, 67.009%, etc., even though those values are not specifically mentioned. The range of 20% to 30% shall include, for example, the values of 21.0% and 28.009%, etc., even though those values are not specifically mentioned.

The term "about," such as "about 20%" or "about pH 7.6," shall mean±5%, ±10% or ±20% of the value given.

EXEMPLIFICATION

Abbreviations and Nomenclature

FFP—Fresh Frozen Plasma manufactured from CPD Whole Blood; plasma not filtered. Plasma is placed in −18° C. freezer within 8 hours of collection.

CP: control plasma, referring to plasma before spray drying

CP/FFP: FFP control plasma

Batch—represents a unique spray drying run at Velico.

SpDP/FFP—Spray dried plasma manufactured from thawed FFP

SpD: spray-drying

SpDP: spray-dried plasma

Feed plasma: liquid plasma to be fed through a feeding tube to spray-drying device Fed plasma: liquid plasma having been fed to the system without being sprayed Sprayed plasma: fed plasma subjected to aerosolization vWF: von Willebrand factor vWF:RCo: vWF activity measured by vWF ristocitein assay PreT: pretreatment or pre-treated (formulation or formulated)

CA: citric acid

PreT/CA: pre-treated (formulated) feed plasma with citric acid

RS-CA: citric acid rehydration solution (3.5 mM citric acid)

RS-CAP: citric acid rehydration solution, buffered with sodium phosphate (pH 3.5)

WFI: water for injection

SDSAS: spray dry stable acidic substance

Example 1

Figure 5:
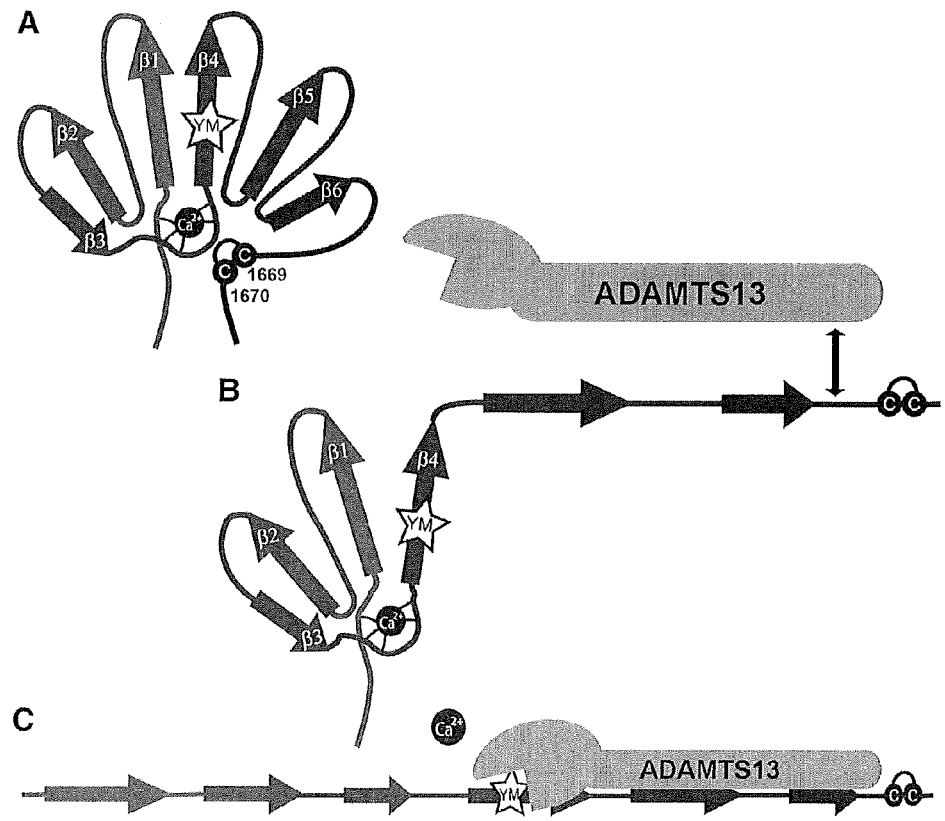
FIG. 5 (A-C) are schematic illustrations depicting unfolding/refolding model of the vWF A2 domain and protelolysis by ADAMTS13.

Enhancing in-Process (Spray-Drying) Stability of vWF Factor and Storage Stability of Multiple Plasma Proteins by Treating the Feed Plasma with Citric Acid Prior to Spray Drying Introduction von Willebrand factor (vWF) is a large adhesive glycoprotein with established functions in hemostasis. It serves as a carrier for factor VIII and acts as a vascular damage sensor by attracting platelets to sites of vessel injury. The size of vWF is important for this latter function, with larger multimers being more hemostatically active. Functional imbalance in multimer size can variously cause microvascular thrombosis or bleeding. The regulation of vWF multimeric size and platelet-tethering function is carried out by ADAMTS13, a plasma metalloprotease that is constitutively active. It is secreted into blood and degrades large vWF multimers, decreasing their activity. Unusually, protease activity of ADAMTS13 is controlled not by natural inhibitors but by conformational changes in its substrate, which are induced when vWF is subject to elevated rheologic shear forces. This transforms vWF from a globular to an elongated protein. This conformational transformation unfolds the vWF A2 domain and reveals cryptic exosites as well as the scissile bond. To enable vWF proteolysis, ADAMTS13 makes multiple interactions that bring the protease to the substrate and position it to engage with the cleavage site as this becomes exposed by shear forces (FIG. 5). ADAMTS 13 (a disintegrin and metalloproteinase with a thrombospondin type 1 motif, member 13), also known as von Willebrand factor-cleaving protease (vWFCP), is a zinc-containing metalloprotease enzyme.

During spray drying (SpD), the plasma proteins are subject to considerable shear forces due to the spraying mechanism as the solutions are fluidized through a fine nozzle to form the droplets in contact with drying air. FIG. 4a is a schematic diagram showing the various shear forces proteins are subject to during spray drying. The process of unfurling multimeric vWF is expected to be triggered by the hydrodynamic forces of elevated shear stress during SpD in combination with air-liquid interface stress. The shear-induced structural change of vWF, when combined with other physical factors associated with SpD, such as high temperature and/or unfavorable pH as well as the air-liquid interface stress, may lead to protein denaturation (if unfolded vWF fails to refold properly post-SpD) and proteolytic degradation (unfolded vWF exposes proteolytic sites for ADMATS13), impairing the vWF activity in the spray dried plasma (SpDP), as well as other proteins.

Spray drying can be optimized to reduce the protein damage caused by shear force and temperature through mechanical engineering. However, the pH rise is inevitable during SpD due to the loss of $CO_2$, driven by both spraying and drying sub-processes. Further, the elevated pH is particularly undesirable for SpDP during storage. SpDP contains a residual amount of water and an alkaline pH will accelerate protein degradation during storage. Therefore, it is highly desirable to maintain the physiological pH during and post SpD. This can be done by adding a non-volatile spray dry stable acidic substance (SDSAS), preferably a physiologically compatible weak acid such as citric acid or lactic acid, to the liquid plasma to counterbalance the $CO_2$ loss by inhibiting pH rise during SpD and thereby allow SpDP to be stored at a non-alkaline pH. In summary, pretreatment or contemporaneous treatment of plasma with citric acid serves three main purposes: 1) it increases in-process stability of plasma proteins; 2) it increases stability of plasma proteins during storage; and 3) it allows SpDP to be rehydrated with water, eliminating the need for a rehydration solution.

Objectives

The object of this study is to evaluate the impact of a SDSAS formulation of plasma with citric acid on the recovery from SpD and stability during storage of SpDP of vWF and other coagulation factors in SpDP.

Study Design and Methods

Plasma samples were formulated by the addition of citric acid from a 20% stock solution prior to spray drying. Plasma samples were spray dried using a drying gas inlet temperature of 125° C., plasma fluid rate of 10 ml/min, aerosol gas rate of 20 L/min and the exhaust temperature was maintained at 55° C. The clotting factors fibrinogen, Factors V, VII, VIII and IX, von Willebrand factor (vWF), prothrombin time (PT) and activated partial prothromboblastin time (aPTT) were determined after spray drying and after storage at 37° C., room temperature and refrigeration. vWF multimer analysis was carried out at the Blood Center of Wisconsin (BCW) as follows. Plasma samples, loaded at equal vWF:Ag levels (0.2 mU), were analyzed by 0.65% LiDS-agarose gel electrophoresis and western blotting with chemiluminescent detection using the Fujifilm LAS-300 luminescent image analyzer. Densitometry was performed and area-under-the curve calculated. The percentage of low (L), intermediate (I) and high (H) molecular weight (MW) multimers (M) were calculated. Formulated SpDP samples were rehydrated with water for injection (WFI), standard SpDP samples (i.e., control samples without added pretreatment agents as listed here) were rehydrated in Citrate-Phosphate Buffer (CPB).

Results

Figure 6:
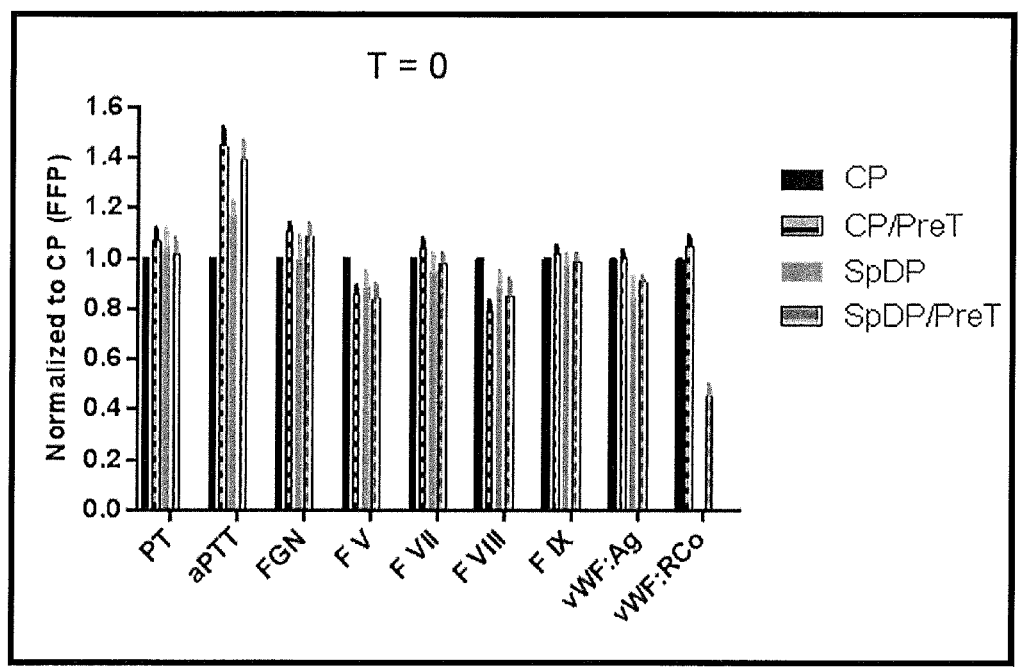
FIG. 6 is a bar graph showing that formulation of plasma with citric acid stabilizes during spray drying ~50% von Willebrand Factor:Ristocetin Cofactor (vWF:RCo) activity without any impact of other coagulation factors. This is done at time zero, time upon completion of spray drying. CP indicates Control Plasma; SpDP indicated Spray-Dried Plasma; PreT indicates plasma formulation with SDSAS.

As shown in FIG. 6, SpD resulted in a loss of coagulation factor activity between 0% and up to 20% (FV, FVII, FVIII and FIX), but had no impact on fibrinogen and vWF antigen levels. However, it lowered the vWF:RCo activity below detection, which, remarkably, increased recovery by 50% by formulation. Consistent with the excellent recoveries of the coagulation factors and fibrinogen, SpD had no adverse effect on PT. SpD slightly prolonged aPTT (comparing Bar 1 and 3 in the aPTT cluster). Citric acid formulation prolonged aPTT of the plasma even before SpD, suggesting that interference of added citric acid in the assay, likely by taking some free calcium required by multi-steps in the intrinsic pathway, collectively measured as aPTT when combined with the common pathway. However, SpD had no impact on aPTT of the formulated plasma (comparing Bar 2 and 4 in aPTT cluster).

Figure 7:
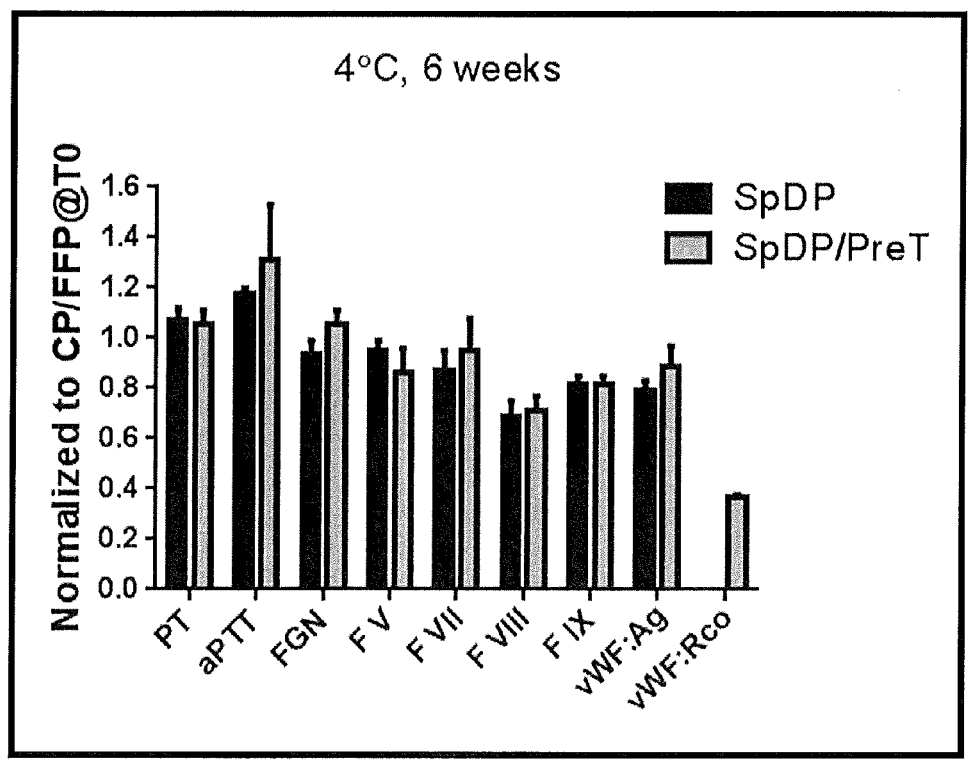
FIG. 7 is a bar graph showing that formulation of plasma with citric acid confers stability to vWF and all other coagulation factors during storage at 4° C.
Figure 8:
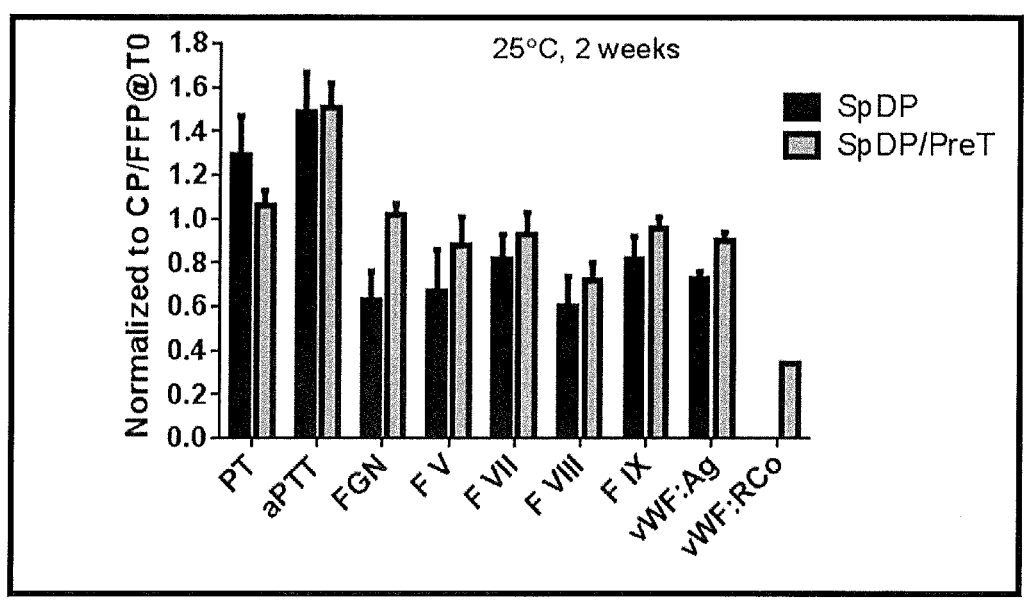
FIG. 8 is a bar graph showing that pre-treatment of plasma with citric acid confers stability to vWF and all other coagulation factors during storage at 25° C.
Figure 9:
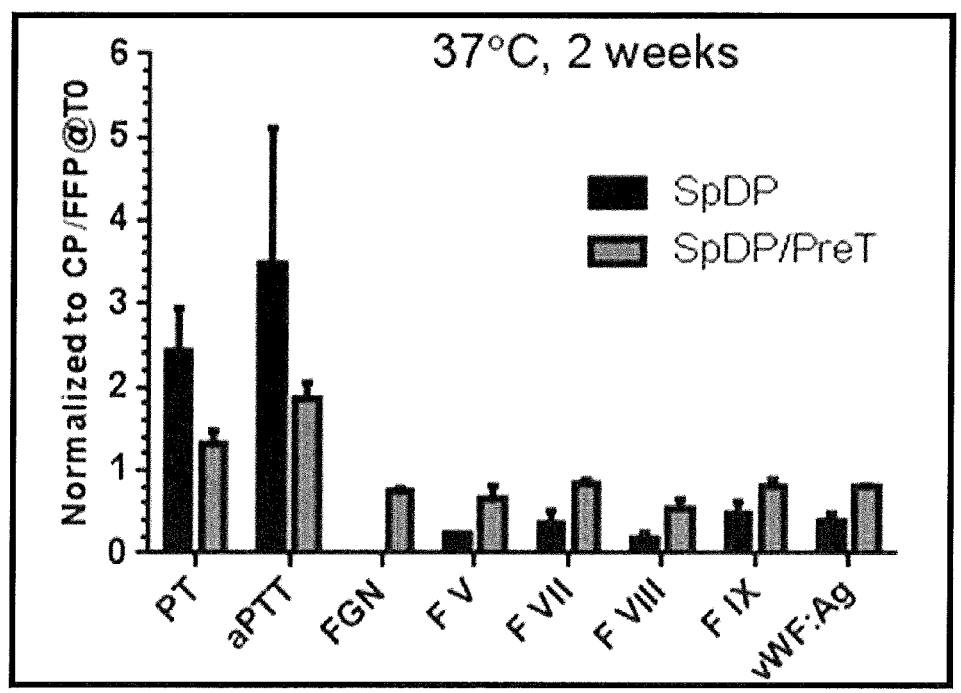
FIG. 9 is a bar graph showing that formulation of plasma with citric acid confers stability to coagulation factors during storage at 37° C.

When stored refrigerated for 6 weeks, coagulation factors in the plasma samples did not lose more than 10% of their activities (FIG. 7.). However, the benefits of Pre-T/CA were highlighted after 2 weeks at 25° C. (FIG. 8) and even more so at 37° C. (FIG. 9). All characterized parameters performed better for Pre-T/CA SpDP than standard SpDP.

Figure 10:
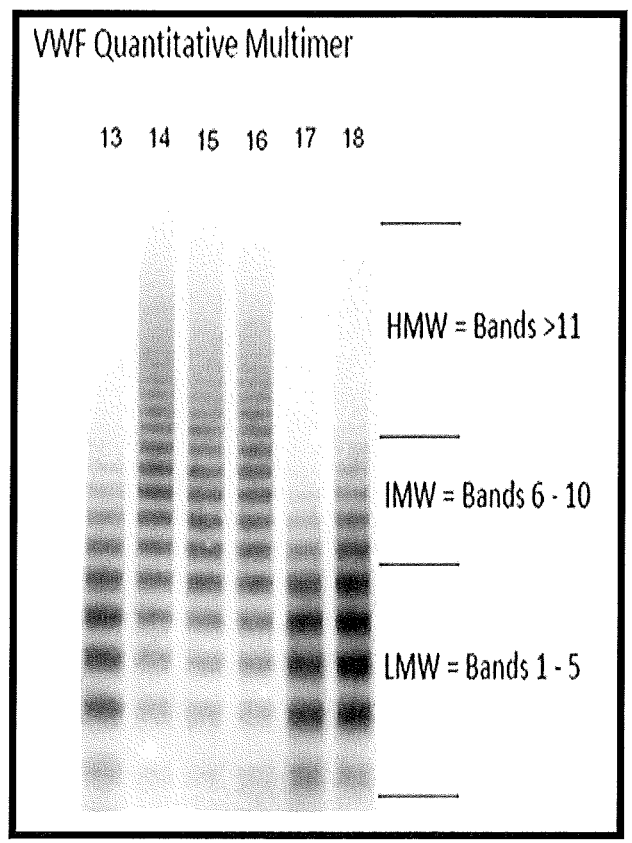
FIG. 10 is a photographic image showing that formulation of plasma with citric acid stabilizes vWF during SpD (spray drying).

To gain insight into steep decline, and dramatic salvage of vWF:RCo activity by plasma formulation, vWF multimer quantifications were performed by the inventors on plasma samples pre and post-SpD, with or without pretreatment. The results are shown in FIG. 10. Positive and negative controls were also included. As rationalized in the introduction to the example, SpD took a heavy toll on vWF multimers, almost completely depleted high molecular weight vWF multimers (HMWM), which was paralleled by an increase in low molecular weight multimers (LMWM). However, Pre-T/CA greatly increased recovery of HMWM multimers, consistent with vWF:RCo data. Lane 13: Type 2B vWF Control=Type 2B von Willebrand disease. Lane 14: Healthy Control. Lane 15: CP=Control plasma. Lane 16: CP/PreT=control plasma plus citric acid. Lane 17: SpDP=reconstituted spray dried plasma. Lane 18: SpDP/PreT=reconstituted spray dried plasma power formulated with citric acid.

Conclusions

Surprisingly, SpD exerts a heavy toll on vWF multimer formation and activity. The results show that vWF is sensitive to shear stress which adversely affects its size and biological function. Shear stress enhances the proteolysis of vWF in normal plasma. Presumably, and while not limiting the present invention to theory, the synergistic effects of shear force during aerosolization, pH change and thermal stress, causes unfolding of vWF. Formulation of plasma with a SDSAS greatly improves the recovery of shear force labile vWF, increases the stability of multiple plasma proteins during storage and simplifies rehydration. SpDP subjected to formulation showed improved profiles of PT, fibrinogen, FV, FVII, FVIII, FIX and vWF antigen (Ag) levels when stored 2 weeks and 4° C. and 25° C.

Example 2

Characterization of the Effect of Aerosol Flow Rate on vWF Factor

Background

The spray-drying process can be divided into feeding, spraying, and drying stages. Each sub-process can potentially cause damage to plasma proteins, especially vWF (FIG. 4). Identification of the critical step(s) to vWF degradation can aid in process development minimizing processing damage to plasma proteins. In this example, the impact of spraying on vWF recovery was evaluated.

Study Design and Methods

Thawed FFP samples were fed at 10 mL/minute under variable aerosol gas flow (0, 5, 10, 15 or 20 L/minute) without drying gas on. These settings, allowing the plasma to be fed into the system, with or without aerosolization in the absence of heating, allowed study of the impact of plasma feeding and spray/aerosol gas flow rate in the spray-drying process. The sprayed liquid plasma samples were analyzed for pH and vWF:RCo.

Results

Figure 11:
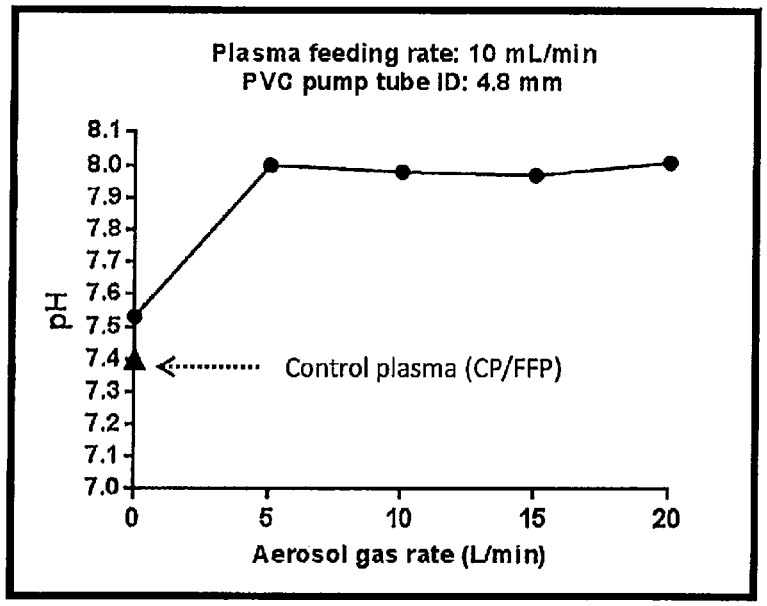
FIG. 11A is a line graph showing pH for CP/FFP and Fed Plasma under constant plasma feeding rate of 10 mL/min, but variable aerosol gas flow rates (0, 5, 10, 15, and 20 L/min).
FIG. 11B is a line graph showing the results activity (IU/dL) of vWF:RCo activity for CP/FFP and the fed plasma under constant plasma feeding rate of 10 mL/min, but variable aerosol gas flow rates (0, 5, 10, 15, and 20 L/min).
Figure 11:
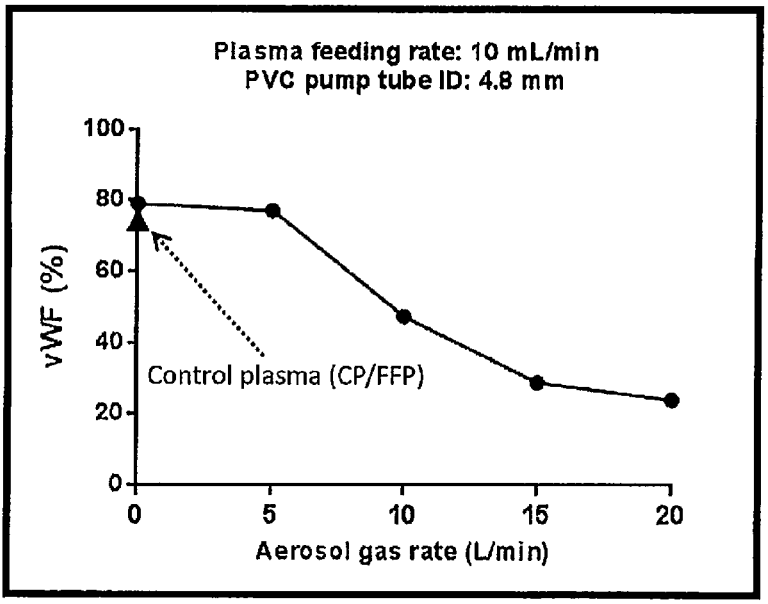

The results are shown in FIGS. 11A and 11B. Plasma feeding at 10 mL/min without aerosol gas flow (0 L/min) allowed the evaluation of the impact of feeding alone on vWF recovery. Plasma feeding alone had no significant impact on either pH or vWF.

vWF still remained intact at 5 L/min of aerosol gas flow, but the pH was sharply elevated to approximately 8.0 (FIG. 11B). However, increase of the aerosol gas flow to 10 L/min eliminated 50% vWF:RCo activity, and suffered more damage as aerosol gas flow increased to 15 and 20 L/min (FIG. 11A). The pH remained at about 8 as the aerosol gas flow was increased from 5 to 20 L/min, indicating near complete loss of $CO_2$ in the plasma upon aerosolization. The lack of correlation between pH rise and vWF:RCo activity at 5 L/min suggests that transient exposure to slight alkaline pH (8.0) alone did not cause detectable damage to vWF.

Escalation of aerosol gas flow downsizes the plasma droplets, which has multiple consequences. The reduced droplet size increased exposure of plasma proteins to air/liquid interfacial stress. The combination of elevated aerosol gas flow and reduced droplet size increased speed of the droplet motion in the gas, thereby aggravating the shear stress to proteins on the droplet surface, which have already been stressed from interaction with the air/liquid interface.

Conclusion

This study firmly established the correlation between aerosolization and vWF factor deterioration.

Example 3

Characterization of the Effect of Plasma Feeding Rate on vWF

Background

Example 2 identified the spray sub-process as a major stress factor responsible for vWF degradation during spray drying. This indicates that the critical negative contribution of the combined shear and air/liquid interfacial stresses was exerted on the plasma droplets (and, consequently, on the plasma proteins) while traveling at a high rate of speed upon aerosolization. It also suggested that the impact of the combined shear and air/liquid interfacial stresses on plasma proteins upon aerosolization can be further modified by altering the droplet size. Droplet size can be modified by varying the plasma feed rate under a constant aerosol flow rate. In this example, plasma was fed into the system at different rates under constant aerosol flow rate. Larger droplets at a higher plasma feeding rate would have less air-liquid interface exposure for plasma proteins and have slower motion rate and lower shear stress for plasma proteins. Thus, the plasma proteins will sustain less stress attributed to air-liquid interface force and shear force.

Study Design and Method

Thawed FFP samples were fed at 2, 4, 6, 8 or 10 mL/min under a constant aerosol gas flow of 10 L/min without drying gas on. The sprayed liquid plasma samples were analyzed for vWF:RCo activity and pH.

Results

Figure 12:
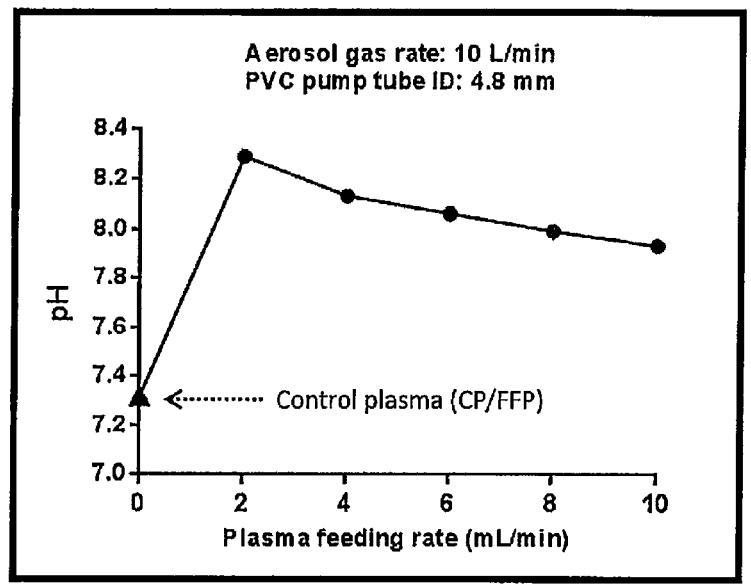
FIG. 12A is a line graph showing pH CP/FFP and Fed Plasma at Aerosol gas flow rates of 10 L/min; fluid=2 ml/min, 10 L/min; fluid=4 ml/min, 10 L/min; fluid=6 ml/min, 10 L/min; fluid=8 ml/min, and 10 L/min; fluid=10 ml/min.
FIG. 12B is a bar graph showing the results activity (IU/dL) of vWF:RCo for CP/FFP and Fed Plasma at Aerosol gas flow rates of 10 L/min; fluid=2 ml/min, 10 L/min; fluid=4 ml/min, 10 L/min; fluid=6 ml/min, 10 L/min; fluid=8 ml/min, and 10 L/min; fluid=10 ml/min.
Figure 12:
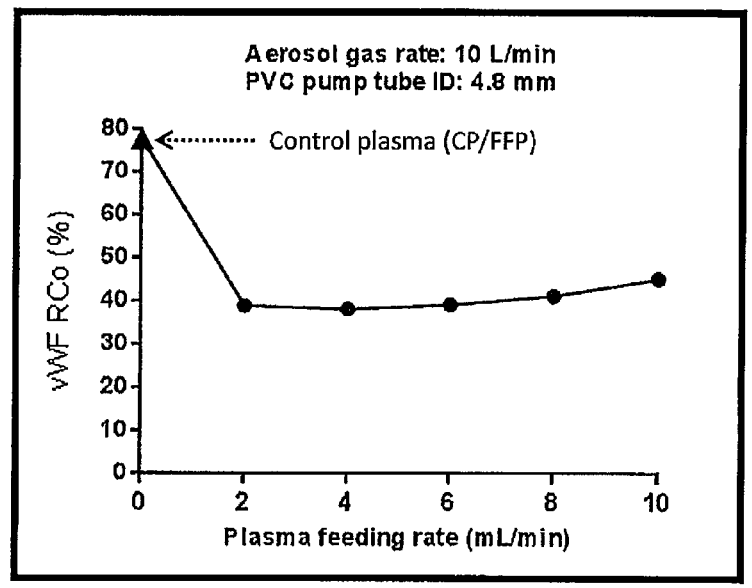

Consistent the observations in Example 2, at 10 L/min of aerosol gas flow, vWF:RCo activity dramatically declined after spraying between 2 and 10 mL/min of plasma input (FIG. 12). vWF:RCo recovery trended slightly higher as plasma input rate increased from 2 to 10 mL/min. pH was significantly increased under all conditions, trending lower from pH 8.3 at 2 mL/min to 7.9 at 10 mL/min as the plasma feed rate increased (FIG. 12B). The opposite trends for pH and vWF:RCo with respect to plasma feeding rate are consistent with the increase of droplet sizes as the result of the increase plasma feeding rate. This reduced the air/liquid-interface to mass ratio and, consequently, the shear and air/liquid-interface stresses as well as $CO_2$ loss.

Conclusion

The results further established the inverse relationship between vWF recovery and spray stresses.

Example 4

The Effect of Formulation of Plasma with Different Spray Dry Stable Acidic Substance (SDSAS's) on vWF Recovery During Spray Background Example 1 highlighted the importance of controlling the pH of the feed plasma in reducing the detrimental effect of spray-drying on vWF. Examples 2 and 3 identified the spray sub-process as a critical step leading to the degradation of vWF. Taken together, these data suggest that reducing the destructive effect of spray on vWF by lowering the pH of feed plasma is critical for improving the overall quality of SpDP. In this example, the impact of pretreatment on the preservation of vWF factor during spray was explored using a diverse panel of SDSAS's.

Study Design and Methods

Aliquots of thawed FFP were formulated separately with a wide range of SDSAS's including ascorbic acid, citric acid, gluconic acid, glycine hydrogen chloride (glycine-HCl), lactic acid and monosodium citrate. The amount of the treating chemical was pre-determined by titrating the unformulated SpDP rehydrated with WFI to ~pH 7.3. Control plasmas include formulated and hyper-formulated (7.4 mM citric acid in Example 1) plasma samples.

Results

Figure 13:
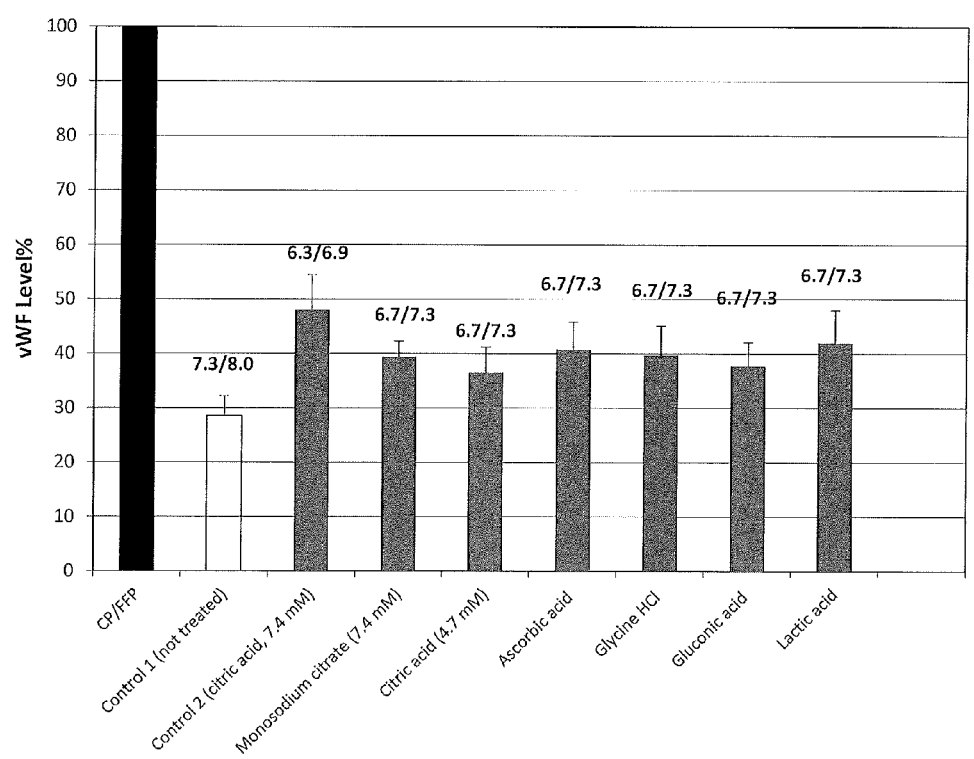
FIG. 13 is a bar graph showing the effect of different SDSAS-formulations on the vWF:RCo recovery and pH during spray. The pH levels prior to and post spray were shown on the top of the bar graph.

The results are shown in FIG. 13. Spraying of the naïve plasma led to a sharp rise in pH (pH 7.3 and 8.0 before and after spraying, respectively; 7.3/8.0, Bar 2) and reduced vWF:RCo activity by about 70% (30% recovery) (Bar 2). Formulation of the plasma with 7.4 mM citric acid, which lowered the pH to 6.3 in the feed plasma and resulted in a lower than the physiological pH after spraying (6.9), reduced by about 50% vWF:RCo activity during spraying (50% recovery) (Bar 3). Formulation with 7.4 mM monosodium citrate, which lowered the pH to 6.7 in the feed plasma and resulted in a physiological pH after spraying lowered vWF:RCo activity recovery by about 40% (Bar 4), which was higher than naïve plasma (Bar 2). Formulation with other SDSAS's, citric acid (4.7 mM, Bar 5), ascorbic acid (Bar 6), glycine HCl (Bar 7), gluconic acid (Bar 8) and lactic acid (Bar 9), all of which lowered the plasma pH to ~6.7 and resulted in a physiological pH (~7.3) after spraying, led to similar vWF:RCo activity recovery of about 40% after spray. Taken together, these results indicated that lowering the pH of feed plasma is critical for preserving vWF during spray.

Conclusion

Enhanced vWF preservation can be achieved by formulating the feed plasma with a wide array of SDSAS's—not only citric acid, but monosodium citrate, ascorbic acid, glycine HCl, gluconic acid and lactic acid, and probably many others meeting the criteria given in the present specification. However, the most important consideration in choosing the proper SDSAS is the suitability for transfusion. Other important factors include availability of USP grade formulation, tolerance for terminal sterilization and interference with standard assays, to name a few. As plasma already contains citric acid (as an anticoagulant), addition of more citric acid to bring the concentration identified in the present invention as being suitable for enhanced plasma protein recovery and stability has the advantage of not introducing a new component to serve as a pH adjuster. Further, citrate is usually rapidly metabolized by the liver. However, rapid administration of large quantities of stored blood may cause hypocalcaemia and hypomagnesaemia when citrate binds calcium and magnesium. This can result in myocardial depression or coagulopathy. Patients most at risk are those with liver dysfunction or neonates with immature liver function having rapid large volume transfusion. Slowing or temporarily stopping the transfusion allows citrate to be metabolized. Administration of calcium chloride or calcium gluconate intravenously into another vein can be used in order to minimize citrate toxicity. Nevertheless, the elevation of citrate in SpDP can be avoided by using alternative SDSAS's such as lactic acid and glycine-HCl. Lactic acid is an important constituent in Ringer's Lactate solution, which is often used for fluid resuscitation after a blood loss due to trauma, surgery, or a burn injury. Glycine-HCL is referenced in the US Pharmacopeia.

Example 5

Enhanced vWF Factor Protection During Spray is Inversely Correlated with the pH Levels of the Feed Plasma Background Results from Example 4, evaluating different chemicals for lowering the pH of the feed plasma, confirmed the generality of the inhibition of pH rise during spay improves vWF:RCo activity recovery. However, it is still striking that vWF factor is better preserved at an acidic pH lower than the physiological pH (7.2-7.4) during the spraying process. Nevertheless, the surprising observation suggested the potential of pH manipulation for further improving vWF factor recovery. In this example, we further evaluated pH of the feed plasma with regard to vWF:RCo activity recovery after spraying. Citric acid and lactic acid were chosen for use in the study.

Study Design and Method

Aliquots of thawed FFP were formulated with different concentrations of citric acid or lactic acid from 20× stock solutions. The amount of the formulation chemicals was pre-determined ensuing a physiological or lower pH level of SpDP when rehydrated with WFI. The formulated samples were determined for pH, sprayed, and the recovered liquid samples were analyzed for pH and vWF:RCo activity.

Results

Figure 14:
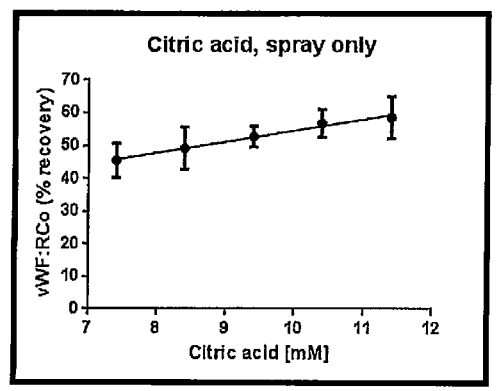
FIG. 14 (A-C) are bar graphs showing the effect of different SDSAS-formulations on the vWF:RCo recovery and pH during spray drying.
Figure 14:
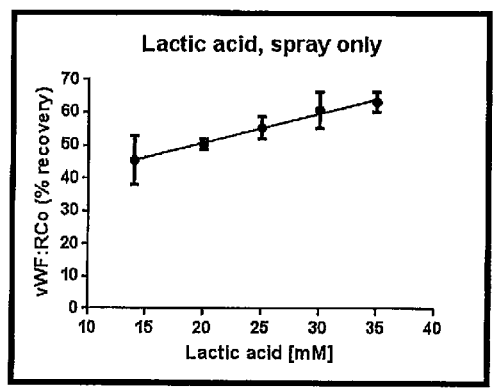
Figure 14:
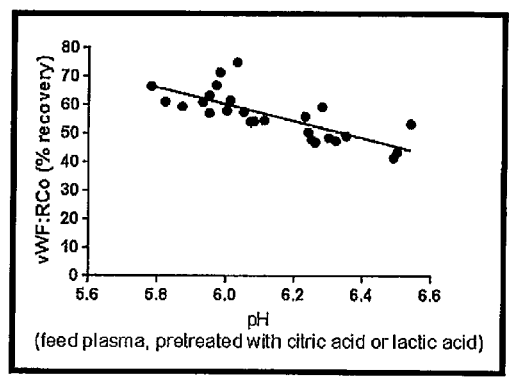

The results are shown in FIG. 14A for citric acid and FIG. 14B for lactic acid. Consistent with earlier observations, spraying alone led to a rise in pH (not shown) and vWF:RCo deterioration under all conditions. Remarkably, vWF:RCo recovery trended higher as the concentration of citric acid or lactic acid increased or pH declined. The inverse correlation between pH of the feed plasma and vWF:RCo activity recovery was clearly shown in FIG. 14C, which was generated by pooling data of both citric acid and lactic acid studies.

Conclusion

Feed plasma pH can be further exploited to increase vWF recovery in conjunction with recovery of other plasma proteins.

What is claimed is:

1. A method of producing spray dried formulated plasma, the method comprising:
   a) providing i) plasma, ii) one or more physiologically compatible spray dry stable acidic substance (SDSAS), wherein said one or more SDSAS is selected from the group consisting of ascorbic acid, citric acid, gluconic acid, glycine hydrogen chloride (glycine-HCl), lactic acid and monosodium citrate, and iii) a spray drying system comprising a spray drier;
b) treating the plasma by adjusting the pH of the plasma with the SDSAS by bringing the concentration of the SDSAS to between about 0.001 and about 0.050 mmol/mL in the plasma to create formulated plasma;
c) drying the formulated plasma with the spray dryer to create spray dried formulated plasma, and determining that the spray dried formulated plasma has a recovery of von Willebrand factor activity at least 5 percentage points greater than the recovery of von Willebrand factor activity obtained from an otherwise identical spray dried plasma that has not undergone treatment with a SDSAS.

2. The method of claim 1, further comprising reconstituting the spray dried formulated plasma with sterile water to produce reconstituted plasma.

3. The method of claim 2, wherein said reconstituted plasma has a pH of about 6.8 to about 7.6.

4. The method of claim 1, wherein said SDSAS is citric acid.

5. The method of claim 1, wherein said SDSAS is lactic acid.

6. The method of claim 1, wherein said pH of said plasma is adjusted with said one or more SDSAS up to 30 minutes before drying, thereby creating the formulated plasma.

7. The method of claim 1, wherein said pH of said plasma is adjusted by adding one or more SDSAS immediately prior to or contemporaneously with drying, thereby creating the formulated plasma.

8. The method of claim 1, wherein the pH of the plasma is known prior to addition of said SDSAS and the amount of said SDSAS to be added plasma is determined based on the known pH of said plasma.

9. The method of claim 1, wherein citric acid is added to the plasma to increase citrate concentration by 7.4 mM.

10. The method of claim 1, wherein said formulated plasma has a pH of about 5.5 to about 6.5.

11. The method of claim 1, wherein said recovery of von Willebrand factor activity is of about 5 to about 40 percentage points greater than the recovery of von Willebrand factor activity obtained from an otherwise identical spray dried plasma that has not undergone formulation with one or more SDSAS.

12. The method of claim 11, wherein said recovery of von Willebrand factor activity is of about 10 to about 35 percentage points greater than the recovery of von Willebrand factor activity obtained from an otherwise identical spray dried plasma that has not undergone formulated with one or more SDSAS.

13. The method of claim 1, wherein said spray dried formulated plasma is stable at ambient temperature for at least 7 days.

14. The method of claim 13, wherein stability of said spray dried formulated plasma is determined by measuring the activity of Factors V, VII, VIII and IX.

15. The method of claim 1, wherein said plasma comprises CPD (citrate phosphate dextrose solution) plasma or is WB (whole blood) plasma.

16. A method of producing spray dried plasma, the method comprising:
a) contacting i) blood plasma contemporaneously with ii) one or more spray dry stable acidic substances (SDSAS), wherein said one or more SDSAS is selected from the group consisting of ascorbic acid, citric acid, gluconic acid, glycine hydrogen chloride (glycine-HCl), lactic acid and monosodium citrate, to create a plasma formulation so that the pH of plasma formulation is between about 5.5 and 7.2 and iii) spray drying the plasma formulation;
b) wherein, when reconstituted, the reconstituted plasma formulation is determined to have a recovered amount of active von Willebrand's factor that is greater than that of the same plasma spray dried and reconstituted that has not been contacted with the spray dry stable acidic substance prior to spray drying.

17. The method of claim 16 wherein said reconstituted plasma has a pH of about 6.8 to 7.6.

18. The method of claim 16 wherein the reconstituted plasma has a physiological pH.

19. The method of claim 16, wherein the reconstitution solution is an alkaline solution.

20. The method of claim 16, wherein the reconstitution solution comprises a substance selected from the group consisting of: sodium bicarbonate, disodium phosphate, and glycine sodium hydroxide.

* * * * *